US008367895B2

(12) United States Patent
Herrmann et al.

(10) Patent No.: US 8,367,895 B2
(45) Date of Patent: Feb. 5, 2013

(54) COMPOSITIONS AND METHODS FOR THE SUPPRESSION OF TARGET POLYNUCLEOTIDES FROM THE FAMILY APHIDIDAE

(75) Inventors: Rafael Herrmann, Wilmington, DE (US); Michael Lassner, Urbandale, IA (US); Albert L. Lu, Newark, DE (US); Mark Nelson, Newark, DE (US); James K. Presnail, Avondale, PA (US); Janet A. Rice, Wilmington, DE (US)

(73) Assignees: Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 892 days.

(21) Appl. No.: 12/351,189

(22) Filed: Jan. 9, 2009

(65) Prior Publication Data
US 2009/0192116 A1 Jul. 30, 2009

Related U.S. Application Data

(60) Provisional application No. 61/108,924, filed on Oct. 28, 2008, provisional application No. 61/021,676, filed on Jan. 17, 2008.

(51) Int. Cl.
*A01H 5/00* (2006.01)
*C12N 15/82* (2006.01)
*C07H 21/04* (2006.01)

(52) U.S. Cl. ........ 800/302; 800/285; 800/286; 800/279; 536/24.5

(58) Field of Classification Search .................. None
See application file for complete search history.

(56) References Cited

U.S. PATENT DOCUMENTS

| | | | |
|---|---|---|---|
| 2003/0150017 A1 | 8/2003 | Mesa et al. | |
| 2005/0095199 A1 | 5/2005 | Whyard et al. | |
| 2006/0021087 A1 | 1/2006 | Baum et al. | |
| 2006/0063174 A1* | 3/2006 | Turner et al. | 435/6 |
| 2006/0075515 A1 | 4/2006 | Luethy et al. | |
| 2006/0200878 A1 | 9/2006 | Lutfiyya et al. | |
| 2006/0272049 A1 | 11/2006 | Waterhouse et al. | |
| 2007/0199100 A1 | 8/2007 | Michaeli et al. | |

FOREIGN PATENT DOCUMENTS

| | | |
|---|---|---|
| EP | 1 818 405 A3 | 8/2007 |
| WO | WO 01/34815 A | 5/2001 |
| WO | WO 01/37654 A2 | 5/2001 |
| WO | WO 02/00904 A | 1/2002 |
| WO | WO 03/052110 A2 | 6/2003 |
| WO | WO 2005/049841 A1 | 6/2005 |
| WO | WO 2005/077116 A | 8/2005 |
| WO | WO 2005/110068 A2 | 11/2005 |
| WO | WO 2006/044480 A2 | 4/2006 |
| WO | WO 2006/045590 A2 | 5/2006 |
| WO | WO 2006/047495 A | 5/2006 |
| WO | WO 2007/003023 A | 1/2007 |
| WO | WO 2007/087153 A2 | 8/2007 |
| WO | WO 2007/095469 A2 | 8/2007 |

OTHER PUBLICATIONS

Dombrovsky et al. 2007, Comprise. Buiochem. Physiol. B. Biochem. Mol. Biol. 146:256-264.*
Agrawal, N., et al., "siRNA-Directed Silencing of Transgene Expressed in Cultured Insect Cells", Biochemical and Biophysical Research Communications, 2004, pp. 428-434, vol. 320, No. 2, Elsevier Science Publishers Ltd., United Kingdom.
Atkinson, H. J., et al., "Engineering Plants for Nematode Resistance," Ann. Rev. Phytopathol, 2003, pp. 615-639, vol. 41.
Bakhetia, M., et al., "RNA Interference and Plant Parasitic Nematodes," Trends in Plant Science, 2005, pp. 362-367, vol. 10, No. 8, Elsevier Science Publishers Ltd., United Kingdom.
Boutla, A., et al., "Induction of RNA Interference in *Caenorhabditis elegans* by RNAs Derived From Plants Exhibiting Post-Transcriptional Gene Silencing", Nucleic Acids Research, 2002, pp. 1688-1694, vol. 30, No. 7.
Gao, B., et al., "The Parasitome of the Phytonematode Heterodera Glycines,", Molecular Plant-Microbe Interactions, 2003, pp. 720-726, vol. 16, No. 8, APS Press, USA.
Gao, B., et al., "Identification of Putative Parasitism Genes Expressed in the Esophageal Gland Cells of the Soybean Cyst Nematode Heterodera Glycines," Molecular Plant-Microbe Interactions, 2001, pp. 1247-1254, vol. 14., No. 10, APS Press, USA.
Urwin, P. E., et al., "Ingeston of Double-Stranded RNA by Preparasitic Juvenile Cyst Nematodes Leads to RNA Interference," Molecular Plant-Microbe Interactions, 2002, pp. 747-752, vol. 15, No. 8.
Zhu, Y. C., et al., Enhanced Esterase Gene Expression and Activity in a Malathion-Resistant Strain of the Tarnished Plant Bug, *Lygus lineolaris*, Insect Biochemistry and Molecular Biology, 2004, pp. 1175-1186, vol. 34, Elsevier Science Publishers Ltd., United Kingdom.
Zhu, Y. C., et al., Comparative Study on Glutathione S-Transferase Activity, cDNA, and Gene Expression Between Malathion Susceptible and Resistant Strains of the Tarnished Plant Bug, *Lygus lineolaris*, 2006, Pesticide Biochemistry and Physiology, pp. 62-72, vol. 87, Elsevier Science Publishers Ltd., United Kingdom.
Database EMBL [online]: Database Access No. DY786966.

* cited by examiner

*Primary Examiner* — Li Zheng
(74) *Attorney, Agent, or Firm* — Alston & Bird LLP

(57) ABSTRACT

Methods and compositions are provided which employ a silencing element that, when ingested by a pest, are capable of decreasing the expression of a target sequence in the pest. In specific embodiments, the decrease in expression of the target sequence controls the pest and thereby the methods and compositions are capable of limiting damage to a plant. Target polynucleotides for specific protein classes and target polynucleotides set forth in SEQ ID NOS:1, 2, 3, 4, 5, 6, 7, 8, 9, 10 or active variants or fragments thereof are provided, wherein a decrease in expression of one or more sequences in the target pest controls the pest. Further provided are silencing elements which when ingested by the pest decrease the level of the target polypeptide and thereby control the pest. Plants, plant part, bacteria and host cells comprising the silencing elements or an active variant or fragment thereof are also provided.

29 Claims, No Drawings

COMPOSITIONS AND METHODS FOR THE SUPPRESSION OF TARGET POLYNUCLEOTIDES FROM THE FAMILY APHIDIDAE

CROSS-REFERENCE TO RELATED APPLICATIONS

This application claims priority to U.S. Provisional Application No. 61/108,924, filed Oct. 28, 2008, and U.S. Provisional Application No. 61/021,676; filed Jan. 17, 2008; both of which are herein incorporated by reference in their entirety.

FIELD OF THE INVENTION

The present invention relates generally to methods of molecular biology and gene silencing to control pests.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 366591seqlist-.txt, a creation date of Dec. 23, 2008, and a size of 44 Kb. The sequence listing filed via EFS-Web is part of the specification and is hereby incorporated in its entirety by reference herein.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera, Homoptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life. Sci.* 59(3): 417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as a pest from the Aphididae family, is capable of decreasing the expression of a target sequence in the pest. In specific embodiments, the decrease in expression of the target sequence controls the pest and thereby the methods and compositions are capable of limiting damage to a plant or plant part. The present invention provides various target polynucleotides from specific polypeptide families as disclosed herein and various target polynucleotides as set forth in SEQ ID NOS:1, 2, 3, 4, 5, 6, 7, 8, 9, 10 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. In specific embodiment, the pest that is controlled is *Aphis glycines*. Plants, plant parts, bacteria and other host cells comprising the silencing elements or an active variant or fragment thereof are also provided.

A method for controlling a pest, such as a pest from the Aphididae family, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant or plant part expressing the silencing element is ingested by the pest, the level of the target sequence is decreased, and the pest is controlled.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Methods and compositions are provided which employ a silencing element that, when ingested by a pest, such as a pest from the Aphididae family, is capable of decreasing the expression of a target sequence in the pest. In specific embodiments, the decrease in expression of the target sequence controls the pest and thereby the methods and compositions are capable of limiting damage to a plant or plant part. In specific embodiments, the present invention provides target polynucleotides which encode a cuticle polypeptide, a dolichyl-di-phosphooligosaccharide-protein glycotransferase, a myosin polypeptide, a proteosome, a tousled-like kinase, a translation initiation factor 4A, and a Sar1 polypeptide. In other embodiments, the target polynucleotides encode an elongation factor, Gq-like G protein alpha subunit, or a translation initiation factor 1A. In other embodiments the target polynucleotides are set forth in SEQ ID NOS:1, 2, 3, 4, 5, 6, 7, 8, 9, 10 or active variants and fragments thereof. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by pests from the Aphididae family.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also the examples below.

The invention is drawn to compositions and methods for protecting plants from a plant pest, such as pests from the Aphidoidea superfamily, or inducing resistance in a plant or plant part to a plant pest, such as pests from the Aphidoidea superfamily. More specifically, members of the family Aphididae comprise an industrially significant group of pests which may limit the growth and seed production of agriculturally important plants as well as serve as vectors for plant associated viruses. As used herein, the term "Aphididae" or "Aphid" is used to refer to any member of the Aphididae family. Accordingly, the compositions and methods are useful in protecting plants against any Aphididae including, for example, peach-potato aphid *Myzus persicae*, the bean aphid *Aphis fabae*, the pea aphid *Acyrthosiphum pisun*, the cabbage aphid *Brevicoryne brassicae*, the grain aphid *Sitobion avenae*, the rose-grain aphid *Metopolophium dirhodum*, the Russian wheat aphid *Diuraphis noxia* (Mordvilko), the English grain aphid *Macrosiphum avenae*, the greenbug aphid *Schizaphis graminum* (Rondani), the carrot aphid *Cavariella aegopodii*, the potato aphid *Macrosiphum euphorbiae*, the groundnut aphid *Aphis craccivora*, the cotton aphid *Aphis gossypii*, the black citrus aphid *Toxoptera aurantii*, the brown citrus aphid *Toxoptera ciidius*, the willow aphid *Cavariella* spp., the corn leaf aphid *Rhopalosiphum maidis*, the aphid *Rhopalosiphum padi*, the willow leaf aphids *Chaitophorus* spp., the black pine aphids *Cinara* spp., the sycamore aphid *Drepanosiphum platanoides*, the spruce aphids *Elatobium* spp., *Aphis citricola*, *Lipaphis pserudobrassicae* (turnip aphid), *Nippolachnus piri*, the foxglove aphid *Aulacorthum solani*, the asparagus aphid *Brachycorynella asparagi*, the brown ambrosia aphid *Uroleucon ambrosiae*, the buckthorn aphid *Aphis nasturtii*, the corn root aphid *Aphis maidiradicis*, the cresentmarked lily aphid *Neomyzus circumflexes*, the goldenglow aphid *Dactynotus rudbeckiae*, the honeysuckle and parsnip aphid *Hyadaphis foeniculi*, the leafcurl plum aphid *Brachycaudus helichrysi*, the lettuce root aphid *Pemphigus bursarius*, the mint aphid *Ovatus crataegarius*, the artichoke aphid *Capitophorus elaeagni*, the onion aphid *Neotoxoptera formosana*, the pea aphid *Macrosiphum pisi*, the rusty plum aphid *Hysteroneura setariae*, the shallot aphid *Myzus ascalonicus*, the solanum root aphid *Smynthurodes betae*, the sugarbeet root aphid *Pemphigus betae*, the tulip bulb aphid *Dysaphis tulipae*, the western aster root aphid *Aphis armoraciae*, the white aster root aphid *Prociphilus erigeronensis*. In particular embodiments, methods control the soybean aphid *Aphis glycines*. In still other embodiments, the pest of interest comprises a species from *Homopera*, such as, white flies.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance the target sequence can be essential for growth and development. While the target sequence can be expressed in any tissue of the pest, in specific embodiments of the invention, the sequences targeted for suppression in the pest are expressed in cells of the gut tissue of the pest, cells in the midgut of the pest, and cells lining the gut lumen or the midgut. Such target sequences can be involved in gut cell metabolism, growth or differentiation.

In one embodiment, the target sequence comprises a polynucleotide encoding a polypeptide belonging to one or more classes of polypeptides such as a cuticle polypeptide, a dolichyl-di-phosphooligosaccharide-protein glycotransferase, a myosin polypeptide, a proteosome, a tousled-like kinase, a translation initiation factor 4A, and a Sar1 polypeptide. In other embodiments, the target polynucleotides encode an elongation factor, a Gq-like G protein alpha subunit, or a translation initiation factor 1A.

Non-limiting examples of target sequences of the invention include a polynucleotide set forth in SEQ ID NO:1, 2, 3, 4, 5, 6, 7, 8, 9, 10 or a biologically active variant or fragment thereof. As exemplified elsewhere herein, decreasing the level of expression of these target sequence in Aphididae controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprises one or more silencing elements to the same or different target polynucleotides.

In specific embodiments, the target sequence is not a plant endogenous gene. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a miRNA, or a hairpin suppression element. Non-limiting examples of silencing elements that can employed to decrease expression of these target Aphididae sequences comprise or consists of fragments and variants of the sense or antisense sequence of the sequence set forth in SEQ ID NO: 11, 14, 17, 20, 23, 26, 29, 32, 35, 38, 41, 44, 47, 50, 53, 56, 59, 62, 65, 68, 71, 74, 77, 80, 83, 86, 89, 12, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 58, 60, 61, 63, 64, 66, 67, 69, 70, 72, 73, 75, 76, 78, 79, 81, 82, 84, 85, 87, 88, 90, 91 or a biologically active variant or fragment thereof.

In specific embodiments, the silencing element comprises or consists of at least one of the sequences set forth in any one of SEQ ID NO:11-91. In some embodiments, the silencing element further comprises at least one additional thymine residue on the 3' end. Such residues can aid in stabilization. In specific embodiments, at least 1, 2, 3, 4, 5, 6, 7, 8, 9, 10 or more thymine residues can be added to the 3' end of the silencing elements. In further embodiments, silencing elements comprise a polynucleotide having SEQ ID NO: 12 and 13; 15 and 16; 18 and 19; 21 and 22; 24 and 25; 27 and 28; 30 and 31; 33 and 34; 36 and 37; 39 and 40; 42 and 43; 45 and 46; 48 and 49; 51 and 52; 54 and 55; 57 and 58; 60 and 61; 63 and 64; 66 and 67; 69 and 70; 72 and 73; 75 and 76; 78 and 79; 81 and 82; 84 and 85; 87 and 88; and/or 90 and 91. In other embodiments, the silencing element is designed to target the sequence set forth in SEQ ID NO: 11, 14, 17, 20, 23, 26, 29, 32, 35, 38, 41, 44, 47, 50, 53, 56, 59, 62, 65, 68, 71, 74, 77, 80, 83, 86, or 89.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 30, 50, 100, 150, 200, 250, 300, 350, 400, 450, 500, 600, 700, 900 or longer.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 25, 50, 100, 200, 300, 400, 450 nucleotides or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

iii. Double Stranded RNA Silencing Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional iRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In one embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 20, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides. In other embodiments, the length of the first and/or the third segment comprises at least 10-20 nucleotides, 20-35 nucleotides, 30-45 nucleotides, 40-50 nucleotides, 50-100 nucleotides, or 100-300 nucleotides. See, for example, International Publication No. WO 0200904. In specific embodiments, the first and the third segment comprises at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 20-35 nucleotides, about 25-50 nucleotides, about 20 to 75 nucleotides, about 40-90 nucleotides about 15-100 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129: 1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments a domain of the silencing element shares sufficient homology to at least about 15 consecutive nucleotides from about nucleotides 1-50, 50-100, 100-150, 150-200, 200-250, 250-300, 300-350, 350-400, 400-450, 450-500, 550-600, 600-650, 650-700, 750-800, 850-900, 950-1000, 1000-1050, 1050-1100, 1100-1200, 1200-1300, 1300-1400, 1400-1500, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In specific embodiments, the silencing element comprising the hairpin comprises a sequence selected from the group consisting of SEQ ID NO: 12 and 13; 15 and 16; 18 and 19; 21 and 22; 24 and 25; 27 and 28; 30 and 31; 33 and 34; 36 and 37; 39 and 40; 42 and 43; 45 and 46; 48 and 49; 51 and 52; 54 and 55; 57 and 58; 60 and 61; 63 and 64; 66 and 67; 69 and 70; 72 and 73; 75 and 76; 78 and 79; 81 and 82; 84 and 85; 87 and 88; and/or 90 and 91.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18 :2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, U.S. Provisional Application No. 60/691,613, filed Jun. 17, 2005, entitled "Methods and Compositions for Gene Silencing, herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins or variant polypeptides that retain biological activity. Thus, fragments of a nucleotide sequence may range from at least about 10, about 15, about 20 nucleotides, about 50 nucleotides, about 75 nucleotides, about 100 nucleotides, about 200 nucleotides, about 300 nucleotides, about 400 nucleotides, about 500 nucleotides, about 600 nucleotides, about 700 nucleotides and up to the full-length polynucleotide (i.e., the target polynucleotide) employed in the invention. Methods to assay for the activity of a desired silencing element or suppressor enhancer element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity. A silencing element or suppressor enhancer element of a variant target sequence need not encodes a protein, but rather will have the ability to reduce the level of expression of the target sequence.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, as discussed elsewhere herein. Such variants may result from, for example, genetic polymorphism or from human manipulation. Biologically active variants of a native protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

V. DNA Constructs

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol.*

*Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11):1779-86), Rice (RSs1) (Shi, T. Wang et al. (1994). *J. Exp. Bot.* 45(274): 623-631) and maize sucrose synthese-1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70., At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2): 141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see

*EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral* (BMC) *Biotechnology* 3:7; Graham et al. (1997) *Plant Mol. Bial.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. 1994) *J. Exp. Bot.* 45:623-31); the CoYMV or Commelina yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from Arabidopsis shown to have phloem-specific expression in tobacco by Kertbundit et al. 1991) *Proc. Natl. Acad. Sci. USA* 88:5212-16); the VAHOX1 promoter region (Tomero et al. 1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultrl; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10: 143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element and/or suppressor enhancer element can be provided as an external composition such as a spray or powder to the plant, plant part, seed, a pest, or an area of cultivation. In another example, a plant is transformed with a DNA construct or expression cassette for expression of at least one silencing element. In either compositions, the silencing element, when ingested by an insect, can reduce the level of a target pest sequence and thereby control the pest (i.e., any pest from the Aphididae family, such as, *Aphis glycines*). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3$^{rd}$ ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella,* and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a pest from the Aphididae family) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91:2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereals*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

Methods for controlling a pest (i.e., pest from the Aphididae family, such as, *Aphis glycines*) are provided. The method can comprise feeding to a pest a composition comprising a silencing element of the invention, wherein said silencing element, when ingested by a pest (i.e., pests from the Aphididae family, such as, *Aphis glycines*), reduces the level of a target polynucleotide of the pest and thereby controls the pest. The pest can be fed the silencing element in a variety of ways. For example, in one embodiment, the polynucleotide comprising the silencing element is introduced into a plant or plant cell. As the aphid feeds on the plant, part thereof, or plant cell expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In one embodiment, expression in phloem companion cells occurs. Such expression could be achieved employing a tissue specific promoter or a constitutive promoter.

In another method, a composition comprising at least one silencing element of the invention are applied to a plant. In such embodiments, the silencing element can be formulated in an agronomically suitable and/or environmentally acceptable carrier, which are preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and compositions can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. Provisional Application No. 61/021,676, entitled "Compositions and Methods for the Suppression of Target Polynucleotides", filed Jan. 17, 2008 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a fragment or a variant of a polynucleotide encoding a juvenile hormone polypeptide, a vacuolar polypeptide, a cadherin polypeptide, a cuticle polypeptide, a translation initiation factor, a SAR1 polypeptide, an elongation factor, a phosphooligosaccharide, a myosin polypeptide, a potassium channel amino acid transporter, a potassium inwardly rectifier polypeptide, an amino acid transporter, a tubulin polypeptide, a ubiquitin polypeptide, and small nuclear ribonucleoprotein. In still other embodiments, the suppressor enhancer element comprises a polynucleotide set forth in SEQ ID NO: 1, 2, 3, 4, 5, 6, 7, 8, 9, 10 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element results in the systemic production of RNAi throughout the entire plant. In further embodiments, the plant or plant parts of the invention have improved loading of RNAi into the phloem of the plant over what is observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression. Thus, in specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1

Specific Target Genes and Silencing Elements that Cause Insecticidal Activity Against *Aphis Glycines*

Disruption of insect gene function via RNAi can produce specific activity against target insects. This specificity is enhanced by delivery of the dsRNAs via transgenic plants. Identification of gene function in insects via RNAi has been largely limited to injection of dsRNAs. In fact, past experiments have indicated that insects are not capable of systemic RNAi response based on exposure to dsRNAs.

As described below, we have demonstrated acute activity of numerous dsRNA pairs through injection experiments and additionally have demonstrated insect antagonism through ingestion of dsRNAs. This evidence identifies several gene/primer pair combinations with clear insecticidal properties. The use of dsRNAs in transgenic plants also addresses the potential complication of heterologous protein expression and the possible risks of allergic reaction, non-target activity, and environmental- or bioaccumulation. The data presented below represents the first test of disruption of these particular genes resulting in insecticidal activity in whole organisms and the first report of insecticidal activity of dsRNAs against *A. glycines*.

The invention describes specific target genes and the dsRNA sequences causing insecticidal activity against the soybean aphid *Aphis glycines* through RNA interference of the target gene's expression. Disruption of the genes targeted by the dsRNA sequences may be broadly insecticidal in numerous species. The specific dsRNA sequences display insecticidal activity upon ingestion indicating they can be utilized with a transgenic plant mode of delivery. Table 1 provides the polynucleotide of each target sequence from *Aphis glycines*, a brief description of the function of the protein encoded by the target sequence, and a SEQ ID NO. Table 2 and Table 3 provide a summary of primers used to suppress the target polynucleotides. Various assays to test for the pesticidal activity of dsRNA are described below.

Bioassay Testing Pesticidal Activity of dsRNA in Solution Against Aphids

This assay can be used for a variety of homopterans. The assay involves trapping the sample dsRNA between two layers of stretched parafilm which act as a sachet on top of a small vessel containing the insect of choice.

The assay is prepared as follows: 1 cm diameter polystyrene tubing is cut into 1 cm lengths. One end of the tube is then capped with parafilm or a fine mesh screen. The desired number of aphids is then added to the chamber, after which the remaining open end of the chamber is sealed with a finely stretched layer of parafilm. 20 ul of dsRNA resuspended in a solution of 20% sucrose and 0.1% green food coloring (McCormick and Company, Inc.) is added to the top of the parafilm. A second layer of parafilm is then stretched by hand and placed over the sample. The sample is spread between the two layers of parafilm to make a continuous sachet on which the insects feed. The sachet is then covered tightly with a piece of plastic food film to prevent evaporation and produce a slightly pressurized sample.

Bioassay Testing Pesticidal Activity of dsRNA Expressed by Plants Against Aphids Aphid assays can be run in individual enclosures or in open systems if movement between plants can be prevented. Alternatively, a single leaf may be detached and enclosed in a container such as a Petri dish or microtiter plate. The preferred method is a whole plant assay in individual containers. When transgenic soybeans are used as the sample plant, the chamber should allow for sufficient growth for the duration of the assay.

The assay is prepared as follows: T0 transgenic events are transferred to 4 in. square pots and grown to a height of 6-8 inches. A mylar sheet is formed into a 4 in. diameter×16 in. high cylinder and embedded into the soil of the pot to a depth of 1 inch. 10 adult aphids are then transferred either individually or as a leaf clipping to the inside of the cylinder and the cylinder is sealed with 2 tissue papers secured with two rubber bands. After 1 week, the assay is scored for aphid mortality and/or reproduction.

Soybean Aphid Feeding Assay

Soybean aphids were assayed through the traditional parafilm satchet methodology. The sample of interest was added to 20% sucrose 0.1% green food coloring (McCormick and Company inc.). Data from this assay is shown in tables 2 and 3.
1. The sample was resuspended in 20% sucrose 0.1% green food coloring (McCormick and Company inc.) solution.
2. One end of 1 cm long×1 cm wide section of polystyrene tubing was sealed with parafilm or a fine mesh.
3. The desired number of aphids was added to the polystyrene tubing.
4. The open end of the tubing with a section of finely stretched parafilm was added.
5. A 20 ul droplet of sample was added to the top of the finely stretched parafilm.
6. A second piece of parafilm was held and stretched between one's hands.
7. This second parafilm membrane was placed over the sample thereby capturing the sample between the two parafilm membranes and creating the satchet.
8. The satchet was sealed with a piece of saran wrap to prevent evaporation.
9. After 5 days the number of aphids was counted and reproduction and mortality was determined.

Whole Plant Aphid Assay

Aphid assays can be run in individual enclosures or in open systems if movement between plants can be prevented. A third alternative is to detach a single leaf and enclose the leaf in a container such as a Petri dish or microtiter plate. The preferred method is a whole plant assay in individual containers. For transgenic soybeans the chamber should allow for sufficient growth for the duration of the assay. The method is described below.
1. $T_0$ transgenic events are transferred to 4" square pots (soil, fertilizer, light, temp humidity).
2. Plants are assayed when they reach a height of 6-8 inches.
3. A mylar sheet is formed into a 4 d×16 h" cylinder and embedded in the 4" pot to a depth of 1 inch.
4. 10 adult aphids are then transferred either individually or as a leaf clipping to the container.
5. The top of the cylinder is sealed with 2 tissue papers held in place with two rubber bands.
6. The assay is scored for aphid mortality and or reproduction after 1 week.
7. Upon completion of the bioassay, plants are fumigated and held for production of T1 seed.

TABLE 1

Target Polynucleotides from *Aphis glycines*.

SEQ ID NO: 1

\>iag1c.pk005.i6
TATTTTTATTTTGCTCATAGTCCATAGATTTTATTTATCATTAATTTAGTTTAGGTATATTGTGTACATAATATA
AATTATCTGTTTTTCTACTACGACGCTTCGTTAGGGACTTTGTTGGTAACGTAGCTGTCTTCACTTTTCGTCGGC
CCAGACGCACAGTGAGAATCGAATTGTGGCCAACAATAATTGTTACGACATCAAAACTTTTTACCAATGAACGAC
ATTAAGTTGTGACACTGATTTACTGTACATATTACTATTTTTAAAGATAATTTCATCAAAAAATGTTTCTTTGGG
ATTGGGTTACTGGCGTTCTGGGATATTTAGGACTGTGAAAAAATCAGGAAAACTTCTATTCCTTGGTTTAGATAA
TGCTGGAAAAACTACTTTATTACATATGTTGAAAGATGATCGTTTGGCACAACACACTCCAACATTACATCCAAC
ATCTGAGGAATTGTCTGTTGGAAACATAAAATTCACAACGTTTGATTTGGGTGGCCATTCACAAGCAAGAAAAGT
ATGGAAAGATTATTTCCCTGCTGTAGATGCAATTGTATTTTTGGTAGACGCTTGTGACAAATCTAGAATTATGGA
AAGTAAAAATGAATTAGATTCATTATTGCTTGATGAATCCTTAnnnnACTGCCCCnTACTCGTTCTTGGGnnnnA
AAT

SEQ ID NO: 2

\>iag1c.pk007.p22
CTTATTTATTTTATTAAAAAATATGAGCCCTACAGATTAAAAATTGTAATTAAAAATAAGCAAAGTAATACTATT
CTTGATGTTATGTATAATTGAGTACTGGATGAAGGTGTTGATTTTATTGCTGTGTCATCTACTGGAATACTTGAT
GATGTCGAAATTAGGTTGTCAGTGAGTACAATTGTGGCACCGGGACTTAGATTCAACCATTCTGTAGTTGATATC
GAGTTTCCAGAATTGAAATTCGAGTTTTCGGATCCAACAACAATAGTTAAAGTATCATGCAAATTTGATACTTGG
TCTGATAAACGAACACGCTGTGTATAGTTTGTATCCATATTGATCATTAATGTGTAGTTCTCATGTCCATGCAAA
AATCTGGTTAAAACAAACACTGTATTATTGTTAAGAACATCAATCGCCAACCCTCCTTTTTTAAACGTTTCAGTC
TGGCGTAATTTCGATATGGATTTGAAAAAGTTTAAATAACTTTTAnnATTTTTATTTTCCGTCTGCACGTTTCTC
GTGACATAATCTGGGTGTATCGCAACCCACGGTTCATGTGTGCTATTAGTGAACCCTGCATTTTTCGTATCATCC
CACTGCATAnnACTTCTTGCATAATTGATTTTATCTGATGTATCTTCCATACCAATTTnnnCnnnATATnnnCTA
TnnnTAnnnnnnnnnnnnnTnn

SEQ ID NO: 3

\>iag1c.pk007.h2
TGGTGATAAGGAATTACAATCTAACAATCTTGCTCTCAGCTATGTAGCTAAGCAATTTGTGTTTACCACCACTGT
AAATGATAATAAATTATTTGGCGGCTCGGTTTTCCAAAAATTATCTGATAAATTGGATTTGGGCTTGCAAGTTTC
TTGGTCATCTGAAAGCAATGATTCTTCACTTGCTGTGGGTTCTCAGTATCAACTAAACCAAGACGTTAAGTTGCG
CGCCAAGATTAACAACAAGAGTCAATTGTGCATAGGCTCTGGCATTAAAGTCAAAGAAGGTGTAACATTGACATT
GGCCAGCTTATTGGAATGTCGTCAATTCAACCAAGGCGGTCATAAATTTGGTATTGGCTTAGAACTTGCTTTGTA
AGCAATACACATGCCAAACTTATTTGTACGTTATGTAGACAAAATGTATTGTCAGTAAACGTAGGATTATTAAAC
ATAATCATAAGAGTATTTTTACTACATTAAATAATTCAGTGTGTATTTGTTTAAAATTAATTAGGAAAAATATAA
TTTATATCAGTTGCTCTCGTTAnnnnnnnnnnnnnnnnnnnnnnnnnnnnnnnnnnAn

SEQ ID NO: 4

\>iag1c.pk003.n7
CCCACGCGTCCGAAGTTATTGTCCTTAACCACCCAGGTCAAGTTGGTGCTGGTTACTCACCAGTTCTTGACTGTC
ACACCGCCCACATTGCTTGTAGATTCTCAGAGCTCGTTGAGAAGATCGACAGACGTACCGGTAAGACCCTCGAAG
CTTCACCAAAGTTCGTCAAGTCAGGTGATGCTGCCATCGTCAAGCTCGTTCCAACCAAGCCAATGTGTGTTGAGA
CTTACAACGAGTACCCACCACTCGGTCGTTTCGCTGTCCGTGACATGCGTCAAACCGTTGCTGTTGGTGTCATCA
AGTCTGTTGAGAAGACTGAAAAGGGTGGTAAGACCACCAAGGCTGCTGAAAAGGCAGGTAAGAAGAAGTAAACTC
CAAACGTTCAGCTATCTTAGTTGCGCGCTGGTGCAAAATTTCTCTTTGTCTCTCACGTGTTAAAAATGAAATGCA
TAAGTTCTCCTTAAT TABLE 1-continued Target Polynucleotides from *Aphis glycines*.

SEQ ID NO: 5
>iag1c.pk007.e11
CCCACGCGTCCGGATCGCAGGCGCGAATACCAGCTCACAGATTCTGCTAAATATTATTTAATGGAAATAGACAGA
GTGGCCAGTCCAAATTATCTGCCCACAGAACAAGACATACTTAGAGTAAGGGTACCCACGACGGGCATTATCGAA
TACCCGTTCGATCTAGAAGAAATTCGGTTTAGGATGGTTGATGTTGGAGGCCAGAGATCAnnnnGACnnnnnTGG
ATTCACTGTTTTGAGAATGTAACATC SEQ ID NO: 6
>iag1c.pk001.c6
ACAAACGAAGAACTGAAACACCAATTAAGCAGTCAACAGAAAACAATCGAACAGCACAAGTCACACATAAATAAG
TGCATTGAAGTGGTGAAGAAGCTATTGAAAGAAAAGTCAAATATTGAAAAAAAGAAGCAAGACAGCGGTGTATG
CAAAACAGACTTCGGCTTGGCCAGTTTGTAACGCAAAGGGTTGGTGCACAATTTCAAGAAAATTGGACTGATGGC
TATGCGTTTCAAGAATTGTCTAGAAGACAAGAAGAAATAACGTCAGAAGAGAAGAGATTGACCGACAGAAAAAG
ATGTTGGTCAAAAAACGGCCATCAAACAGTGAAACTGGTGGACGCAAACGAGCTAGTAGTCAGTCGGGTACAGGA
AGTAGTAGTTCGAGTACTAACAGTGTACCAATCAATTCGACGCCTTCAGTTTCTACACCACCTATAACGCTACCC
AGTGCAAGTATCAACAATAACCAAGTTACTGGTGCTACAACAGGCACGGTCTTGCACAACGGCACTGTAGCCCCA
TCGTCCGCCTTGGACACAGCAACGTTCCTAAAGCCAGAAGCTGTTCCGGGTTTATCGTGGCAAGAGTATTACGAA
GCAG SEQ ID NO: 7
>iag1c.pk001.b9
GTTCTGGGAAATCATTTCTGATGAACACGGCATTGACCCAACTGGAGCCTACCATGGAGACTCTGATCTCCAATT
GGAACGTATTAATGTATACTACAATGAAGCCTCAGGTGGAAAGTATGTACCCCGTGCCATCTTGGTCGATTTGGA
ACCTGGTACCATGGATTCCGTCAGATCTGGACCATTCGGTCAAATTTTCAGACCAGACAACTTTGTCTTCGGACA
GTCTGGTGCTGGAAACAATTGGGCCAAAGGTCATTACACAGAAGGTGCTGAGCTTGTAGATTCAGTATTAGATGT
TGTCAGGAAAGAAGCTGAGAGCTGTGATTGTCTTCAAGGTTTCCAATTGACACATTCCTTGGGTGGTGGTACCGG
TTCTGGTATGGGAACCTTATTGATCTCCAAAATCCGTGAAGAATACCCTGACAGAATTATGAACACATACTCTGT
TGTACCCTCTCCTAAAGTATCAGACACTGTTGTAGAACCCTACAATGCTACTCTTTCAGTTCACCAATTGGTTGA
AAATACTGATGAAACCTATTGTATTGACAACGAAGCCTTGTATGACATTTGCTTCCGTACATTAAAACTCACAAC
ACCAACATATGGTGACTTAAACCACTTGGTC SEQ ID NO: 8
>iag1c.pk003.g7
AAGTGTTATTCTGCGGCGGACGTCGGGCGTTGTATTCATATTCTCTCTGATCGTGTGTGTGAGTAATTTACCGCA
AAAACCCGGATTCTGTACCGTTTTTCGCCCGTTAAAGCGATAAACGTTTATTACACTCGTAAAAACTAATTTTAA
TTGTAAATCGGTCCGAAATGGCATCGGGAGTAACCGTAGCGGATGCGTGCAAAAAGGTCTACGAGGAGATCAAAA
AGGACAAGAAGCACAGGTACGTGGTGTTTCACATCAAGGACGAGAAGCAGATCGACATCGAAGTCATCGGCGAGC
GTAACTCTACTTATGACCTGTTCCTAGAAGACCTACAAAAGGCCGGCCCGCAAGAATGCCGTTACGGTCTATTTG
ACTTTGAGTACACTCACCAGTGTCAAGGCACGTCCGAGAGCTCAAAGAAGCAAAAGCTCTTCTTGCTTTGCTGGT
GCCCAGACACAGCTAAAGTAAAGAAGAAGATGGTCTACTCATCCAGCTACGACGCGCTCAAGAAATCACTGGTTG
GCGTACACAAGGCGTTCCAGGCTACTGACCATTCGGAAGCTTCCCAAGAAGTCATCGAGGAGAAGCTCAGGTCCA
CCGACAGACAGTAAA SEQ ID NO: 9
>iag1c.pk001.j9
CGGTCCGCTTCGATGTATATACGCGCAACCGGCGGTCGTTAGTGCGGTTTTTTTTATCGTTTTAACGTATATATA
TATATATTTATATATATTATATATGTACATGTATATACACAAGTAATAATATACACAGCAAAGTATAAATAT
ATATAATTGTATTATATAAATATATACAGCCAGTGTTTTAAATACCGATCTACCGTCGCAAAGAATCGTAAAAAG
AAAAATTGTTTTTCATTTGAAAATATATTCGGTACATTTTTCTATGGTGCACCGTCCGGTAGTTGTAGTACCGTC
GAGATAACTCCTTTGAATATCGAACTCTAAACGCATTCGTCGACGACCGTCGCGAAGTAATAAAACACCCGCAGT
GCTGTTTCCAAATGATGACCATGAACAACCATTCGAACGACATCGACTACAGTAACGGATACATGGAACCGGAAG
AGGAATGGGAACGGGAAGGGCTGTTGGACCCAGCATGGGAAAAACAACAGAAAAAGACCTTTACAGCATGGGGCA
ACTCGCACTTACGTAAAGCAGGTACAGCCATTGAGAACATTGAAGAGGACTTCCGCAATGGGCTCAAACTCATGT
TGCTCCTTGAnn SEQ ID NO: 10
>iag1c.pk001.l15
TAGGACCGTAGTGCCGAAACCGTTTAGTGACTACTAACTAGTAAATATGACAATTTTGTTATGCTAGTAAATACT
AAGTAGGTCCACAAGTACAAGTAACATAGTTGGAACGAACGAAATACGATGACTCAATTTCTACCACCCAATTTG
TTGGCGCTTTTCGCGCCGAGGGATCCAGTCCCTTACCTGCCGCCAGTTGCCAAATTACCGCACGAGAAGAAGACT
CGCGGGTATCTGGGCGTCGGAAGTTTTATGGATTTATTCGAAGATCCCGAAGACACTCCTCCTCCAACAAAAATT
GAAACCCGAGAAGAACGACTAGAACGCCGTCGTCGAGAGAAGGCTGAACAGGTAGCATACAAGTTAGAACAAGAA
ATTGCTTTATGGGAACCACATTCAGTTGCAAACGCTACTACAGATCCATTCAAAACATTATTTGTTGCTAGAATT
AATTATGATACATCTGAATCAAAATTACGAAGAGAATTTGAACTTTACGGTCCTATAAAAAAGATTGTTGTCACA
CATAATAAGATTGATGGTAAACCGAGAGGGTATGCTTTCATTGAGTACGAATATGAACGTGATATGCATTCTGCA
TATAAACATGCTGATGGAAnnn

TABLE 2

| Gene | id | | Targeted region | sense strand |
|---|---|---|---|---|
| Cuticle protein | iag1c.pk003.c6 | active | 5'AAACTATCAAAGTAGACACCATT 3' | ACUAUCAAAGUAGACACCA |
| dolichyl-di-phosphooligosaccharide-protein glycotransferase | iag1c.pk007.f19 | active | AATCAGCACGATGACCCTACATT | UCAGCACGAUGACCCUACA |
| elongation factor | iag1c.pk003.n7 | active | AAGCCAATGTAGTGTTGAGACTT | GCCAAUGUAGUGUUGAGAC |
| | | active | AACTCCAAACGTTCAGCTATCTT | CUCCAAACGUUCAGCUAUC |
| | | | AATGAAATGCATAAGTTCTCCTT | UGAAAUGCAUAAGUUCUCC |
| Gq-like G protein alpha subunit | iag1c.pk007.e11 | | AAGGGTACCCACGACGGAGCATT | GGGUACCCACGACGGAGCA |
| | | | AAGAAATTCGGTTTAGGATGGTT | GAAAUUCGGUUUAGGAUGG |
| Myosin | iag1c.pk007.o21 | active | AAAGGAACACGTGTGCTTTCTT | AGGAAACACGUGUGCUUUC |
| | | | AAGAGAACACTGCAAAATGAGTT | GAGAACACUGCAAAAUGAG |
| | | active | AACAAGATTCGAAGACCCTTATT | CAAGAUUCGAAGACCCUUA |
| proteosome | iag1c.pk006.o6 | | AATTTGCACATGGAGATGATCTT | UUUGCACAUGGAGAUGAUC |
| | | | AACGTCCATATGGAGTTGGTCTT | CGUCCAUAUGGAGUUGGUC |
| | | | AAGGAAGCAAGTTTGGAGGAATT | GGAAGCAAGUUUGGAGGAA |
| tousled-like kinase | iag1c.pk001.c6 | | AACGAAGAACTGAAACACCAATT | CGAAGAACUGAAACACCAA |
| | | | AACAGACTTCGGCTTGGCCAGTT | CAGACUUCGGCUUGGCCAG |
| | | | AATTGGACTGATGGCTATGCGTT | UUGGACUGAUGGCUAUGCG |
| | | | AATCAATTCGACGCCTTCAGTTT | UCAAUUCGACGCCUUCAGU |
| translation initiation factor 1A | iag1c.pk007.b12 | | AAAAGATACTGAGCTAGTGAGTT | AAGAUACUGAGCUAGUGAG |
| | | active | AAAGATACTGAGCTAGTGAGTTT | AGAUACUGAGCUAGUGAGU |
| | | active | AATGAAACAGAAAAGCGTGAGTT | UGAAACAGAAAAGCGUGAG |
| | | | AATGCTCAAGTTACCAAAATGTT | UGCUCAAGUUACCAAAAUG |
| | | | AAGATACAAAAGCCGATGTAATT | GAUACAAAAGCCGAUGUAA |
| translaton initiation factor 4A | iag1c.pk002.a3 | Active | AAATACAGCGTTCAAAAACGATT | AUACAGCGUUCAAAAACGA |
| putative Sar1 protein | iag1c.pk005.i6 | active | AATGATTTCTTTGGGATTGGGTT | UGAUUUCUUUGGGAUUGGG |
| | | active | AATCAGGAAAACTTCTATTCCTT | UCAGGAAAACUUCUAUUCC |
| | | | AACGTTTGATTTGGGTGGCCATT | CGUUUGAUUUGGGUGGCCA |
| | | active | AATTGTATTTTTGGTAGACGCTT | UUGUAUUUUUGGUAGACGC |

| Gene | id | antisense strand | SEQ ID NO |
|---|---|---|---|
| Cuticle protein | iag1c.pk003.c6 | UGGUGUCUACUUUGAUAGU | 11/12/13 |
| dolichyl-di-phosphooligosaccharide-protein glycotransferase | iag1c.pk007.f19 | UGUAGGGUCAUCGUGCUGA | 14/15/16 |
| elongation factor | iag1c.pk003.n7 | GUCUCAACACUACAUUGGC | 17/18/19 |
| | | GAUAGCUGAACGUUUGGAG | 20/21/22 |
| | | GGAGAACUUAUGCAUUUCA | 23/24/25 |
| Gq-like G protein alpha subunit | iag1c.pk007.e11 | UGCUCCGUCGUGGGUACCC | 26/27/28 |
| | | CCAUCCUAAACCGAAUUUC | 29/30/21 |
| Myosin | iag1c.pk007.o21 | GAAAGCACACGUGUUUCCU | 32/33/34 |
| | | CUCAUUUUGCAGUGUUCUC | 35/36/37 |
| | | UAAGGGUCUUCGAAUCUUG | 38/39/40 |
| proteosome | iag1c.pk006.o6 | GAUCAUCUCCAUGUGCAAA | 41/42/43 |
| | | GACCAACUCCAUAUGGACG | 44/45/46 |
| | | UUCCUCCAAACUUGCUUCC | 47/48/49 |
| tousled-like kinase | iag1c.pk001.c6 | UUGGUGUUUCAGUUCUUCG | 50/51/52 |
| | | CUGGCCAAGCCGAAGUCUG | 53/54/55 |
| | | CGCAUAGCCAUCAGUCCAA | 56/57/58 |
| | | ACUGAAGGCGUCGAAUUGA | 59/60/61 |
| translation initiation factor 1A | iag1c.pk007.b12 | CUCACUAGCUCAGUAUCUU | 62/63/64 |
| | | ACUCACUAGCUCAGUAUCU | 65/66/67 |
| | | CUCACGCUUUUCUGUUUCA | 68/69/70 |
| | | CAUUUUGGUAACUUGAGCA | 71/72/73 |
| | | UUACAUCGGCUUUUCUAUC | 74/75/76 |
| translaton initiation factor 4A | iag1c.pk002.a3 | UCGUUUUUGAACGCUGUAU | 77/78/79 |
| putative Sar1 protein | iag1c.pk005.i6 | CCCAAUCCCAAAGAAAUCA | 80/81/82 |
| | | GGAAUAGAAGUUUUCCUGA | 83/84/85 |
| | | UGGCCACCCAAAUCAAACG | 86/87/88 |
| | | GCGUCUACCAAAAAUACAA | 89/90/91 |

(Note:
the sense RNA primer sequence and the antisense RNA primer sequences shown in table 4 were generated having 2 thymine residues at the 3' end.)

TABLE 3

Data from the soybean Aphid Assay described above.

| dsRNA # | Target | id | Assay 1 1.0 uM | Assay 2 1.0 uM | Assay 3 1.0 uM | Assay 4 1.0 uM |
|---|---|---|---|---|---|---|
| sucrose control | SBA | | no | no | no | no |
| Tris control | SBA | | no | no | no | no |
| 0001 | SBA | iag1c.pk003.c6 | no | no | no | moderate |
| 0002 | SBA | iag1c.pk007.f19 | no | no | no | moderate |
| 0003 | SBA | iag1c.pk003.n7 | no | no | no | no |
| 0004 | SBA | iag1c.pk003.n7 | moderate | no | no | no |
| 0005 | SBA | iag1c.pk003.n7 | no | no | moderate | moderate |
| 0006 | SBA | iag1c.pk007.e11 | moderate | no | no | moderate |
| 0007 | SBA | iag1c.pk007.e11 | no | no | severe | severe |
| 0008 | SBA | iag1c.pk007.o21 | no | no | no | no |
| 0009 | SBA | iag1c.pk007.o21 | no | no | no | no |
| 0010 | SBA | iag1c.pk007.o21 | no | no | severe | no |
| 0011 | SBA | iag1c.pk006.o6 | no | no | no | no |
| 0012 | SBA | iag1c.pk006.o6 | no | no | no | no |
| 0013 | SBA | iag1c.pk006.o6 | no | no | severe | no |
| 0014 | SBA | iag1c.pk001.c6 | severe | no | no | severe |
| 0015 | SBA | iag1c.pk001.c6 | severe | severe | severe | severe |
| 0016 | SBA | iag1c.pk001.c6 | no | severe | severe | severe |
| 0017 | SBA | iag1c.pk001.c6 | severe | severe | no | no |
| 0018 | SBA | iag1c.pk007.b12 | moderate | severe | no | no |
| 0019 | SBA | iag1c.pk007.b12 | severe | severe | no | severe |
| 0020 | SBA | iag1c.pk007.b12 | moderate | no | no | no |
| 0021 | SBA | iag1c.pk007.b12 | no | severe | no | severe |
| 0022 | SBA | iag1c.pk007.b12 | no | no | severe | severe |
| 0023 | SBA | iag1c.pk002.a3 | no | no | no | no |
| 0024 | SBA | iag1c.pk005.i6 | severe | no | no | severe |
| 0025 | SBA | iag1c.pk005.i6 | moderate | no | no | severe |
| 0026 | SBA | iag1c.pk005.i6 | moderate | severe | no | severe |
| 0027 | SBA | iag1c.pk005.i6 | severe | no | severe | severe |
| 0028 | lamin | | severe | severe | severe | no |
| 0029 | lamin | | severe | severe | no | severe |
| 0030 | SBA | iag1c.pk007.b12 | no | no | no | no |
| 0031 | SBA | iag1c.pk001.b9 | no | severe | severe | severe |
| 0032 | SBA | iag1c.pk001.b9 | no | no | severe | severe |
| 0033 | SBA | iag1c.pk001.b9 | no | no | severe | no |
| 0034 | SBA | iag1c.pk001.l24 | no | no | no | severe |
| 0035 | SBA | iag1c.pk001.l24 | no | no | no | severe |
| 0036 | SBA | iag1c.pk003.g7 | no | no | no | severe |
| 0037 | SBA | | no | no | no | no |
| 0038 | SBA | iag1c.pk003.g7 | nt | severe | no | severe |
| 0039 | SBA | iag1c.pk003.g7 | nt | no | severe | severe |
| 0040 | SBA | iag1c.pk003.g7 | nt | no | severe | no |
| 0041 | SBA | iag1c.pk003.g7 | nt | no | no | no |
| 0042 | SBA | iag1c.pk003.g7 | nt | no | no | no |
| 0043 | SBA | iag1c.pk003.g7 | nt | no | no | no |
| 0044 | SBA | iag1c.pk003.g7 | nt | no | no | no |
| 0045 | SBA | iag1c.pk007.h4 | nt | no | no | no |
| 0046 | SBA | iag1c.pk007.i11 | nt | no | no | no |
| 0047 | SBA | iag1c.pk001.j11 | nt | no | no | no |
| 0048 | SBA | iag1c.pk001.j11 | nt | no | no | no |
| 0049 | SBA | iag1c.pk001.j11 | nt | no | no | severe |
| 0050 | SBA | iag1c.pk001.k11 | nt | no | no | no |
| 0051 | SBA | iag1c.pk001.k11 | nt | no | no | severe |
| 0052 | SBA | iag1c.pk014.m6 | nt | no | no | severe |
| 0053 | SBA | | nt | no | no | severe |
| 0054 | SBA | | nt | no | no | no |
| 0055 | SBA | | nt | no | no | no |
| 0056 | SBA | iag1c.pk004.n16 | nt | no | no | no |
| 0057 | SBA | | nt | no | no | no |
| 0058 | SBA | | nt | no | no | no |
| 0059 | SBA | | nt | no | no | no |
| 0060 | SBA | | nt | no | no | severe |

TABLE 3-continued

| 0061 | SBA | iag1c.pk007.p22 | nt | no | no | severe |
|---|---|---|---|---|---|---|
| 0062 | SBA | | nt | no | no | severe |
| 0063 | SBA | | nt | no | no | severe |
| 0064 | SBA | | nt | severe | severe | severe |
| 0065 | SBA | iag1c.pk001.j9 | nt | no | severe | severe |
| 0066 | SBA | iag1c.pk007.h2 | nt | severe | severe | severe |
| 0067 | SBA | | nt | no | severe | severe |
| 0068 | SBA | | nt | no | no | severe |
| 0069 | SBA | iag1c.pk001.l15 | nt | no | severe | severe |
| 0070 | SBA | | nt | no | severe | severe |
| 0071 | SBA | | nt | no | no | severe |
| 0072 | SBA | iag1c.pk002.c12 | nt | no | no | no |
| 0073 | SBA | iag1c.pk001.n13 | nt | no | no | no |
| 0074 | SBA | | nt | no | no | no |

Table 3 provides are two designations for activity; severe, and moderate. Severe activity is defined as >90% mortality in original aphids and any offspring. Moderate activity is defined as reduced reproduction combined with moderate mortality in original aphids and offspring. Some surviving aphids can be found with sample demonstrating moderate activity.

Example 2

Transformation of Maize

Immature maize embryos from greenhouse donor plants are bombarded with a plasmid containing the silencing element of the invention operably linked to a PP2 promoter from pumpkin and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to a PP2 promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the appropriate marker.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I H₂O after adjusting pH to 5.6); and 6 g/l bacto-agar (added after bringing to volume with polished D-I H₂O), sterilized and cooled to 60° C.

Various feeding assays that you would use to show that plants ingested by the Aphids have insecticidal activity are described above.

Example 3

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).
Soybean Embryogenic Suspension Culture Initiation Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.
Preparation of DNA for Bombardment Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M CaCl₂ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS1000/HE instrument disk. Each 5 μl aliquot contains approximately 0.375 mg gold per bombardment (i.e. per disk).
Tissue Preparation and Bombardment with DNA Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.
Selection of Transformed Embryos Transformed embryos were selected either using hygromycin (when the hygromycin phosphotransferase, HPT, gene was used as the selectable marker) or chlorsulfuron (when the acetolactate synthase, ALS, gene was used as the selectable marker).
Hygromycin (HPT) Selection Following bombardment, the tissue is placed into fresh SB196 media and cultured as described above. Six days postbombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.
Chlorsulfuron (ALS) Selection Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when ingested by Aphididae, to control the Aphididae.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm | pH 5.8

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL-Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL-Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL-Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL-Cat#21153-036); pH 5.7; and, 5 g TC agar.

2,4-D stock is obtained premade from Phytotech cat #D 295—concentration is 1 mg/ml.

B5 Vitamins Stock (per 100 ml) which is stored in aliquots at −20C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide Example 5

Examples of Suppression Constructs of Interest

Soybean aphid miRNA constructs were generated as described below. The miRNA sequence of interest along with the NOS terminator, XmaI, and EcoR1 sites were synthesized by DNA2.0. GUS; NOS cassettes of ubiq3 vector (PHP17474) was substituted with our cassette by Sma1 and EcorR1 digests.

```
Construct #1
LOCUS           PHP35696 5270 bp DNA circular

DEFINITION      UBi3 pro; gmir168.iagic.pk005.i6; NOS term.

SOURCE
  ORGANISM

COMMENT         Component Fragments
                #1: FRAGMENT of PHP17474
                  parent position: from 6394 to 4240 original length: 4853 molecule position: from 1 to 4853
```

-continued

```
            Left Terminus
                EcoRI site #1

Right Terminus
                SmaI site #1

2: FRAGMENT of gmir 168c-iag1c.pk005.i6 with R.Sites
            parent position: from 4 to 420 original length: 417 molecule position: from 4854 to 5270

Left Terminus
                SmaI site #1

Right Terminus
                EcoRI site #1

COMMENT          This file is created by Vector NTI

COMMENT          ORIGDB|GenBank

COMMENT          VNTDATE|472664005|

COMMENT          VNTDBDATE|473182290|

COMMENT          LSOWNER|

COMMENT          VNTNAME|PHP35696|

COMMENT          VNTAUTHORNAME|Mani Muthalagi|

COMMENT          VNTAUTHORTEL|5-1975|

COMMENT          VNTAUTHOREML

COMMENT          VNTREPLTYPE|Plasmid

COMMENT          VNTEXTCHREPL|Bacteria

FEATURES                  Location/Qualifiers

CDS                  1077 . . . 1937

/vntifkey="4"

/label=AMP promoter             3111 . . . 4466

/vntifkey="30"

/label=UBQ3\PRO

/note="UBQ3 promoter isolated from Arabidopsis."

intron               4467 . . . 4841

/vntifkey="15"

/label=UBQ3\INTRON

/note="The first intron at 5'-end of gene"

misc_RNA             4877 . . . 4897

/vntifkey="53"

/label=AG-MSARP

/note="Synthetic sequence complementary to Sar 1
protein from Aphis glycines. This is an artificial microRNA."

misc_RNA             complement(4944 . . . 4964)

/vntifkey="53"

/label=AG-MSARP\STAR\SEQ
```

-continued

/note="synthetic sequence complimentary to sequence AG-MSARP to silence the expression of Sar 1 protein in Aphis glycines. This sequence forms the hairpin in an artificial microRNA precursor."

terminator 4992 . . . 5269

/vntifkey="43"

/label=NOS\TERM misc_RNA 4898 . . . 4943

/vntifkey="53"

/label=GM\MIRNA\PRECURSOR\168C

BASE COUNT 1416 a 1129 c 1149 g 1576 t

ORIGIN (SEQ ID NO: 92)

```
   1 aattcactgg ccgtcgtttt acaacgtcgt gactgggaaa accctggcgt tacccaactt
  61 aatcgccttg cagcacatcc ccctttcgcc agctggcgta atagcgaaga ggcccgcacc
 121 gatcgccctt cccaacagtt gcgcagcctg aatggcgaat ggcgcctgat gcggtatttt
 181 ctccttacgc atctgtgcgg tatttcacac cgcatacgtc aaagcaacca tagtacgcgc
 241 cctgtagcgg cgcattaagc gcggcgggtg tggtggttac gcgcagcgtg accgctacac
 301 ttgccagcgc cctagcgccc gctcctttcg ctttcttccc ttcctttctc gccacgttcg
 361 ccggctttcc ccgtcaagct ctaaatcggg ggctcccttt agggttccga tttagtgctt
 421 tacggcacct cgaccccaaa aaacttgatt tgggtgatgg ttcacgtagt gggccatcgc
 481 cctgatagac ggtttttcgc cctttgacgt tggagtccac gttctttaat agtggactct
 541 tgttccaaac tggaacaaca ctcaacccta tctcgggcta ttcttttgat ttataaggga
 601 ttttgccgat ttcggcctat tggttaaaaa atgagctgat ttaacaaaaa tttaacgcga
 661 attttaacaa aatattaacg tttacaattt tatggtgcac tctcagtaca atctgctctg
 721 atgccgcata gttaagccag ccccgacacc cgccaacacc cgctgacgcg ccctgacggg
 781 cttgtctgct cccggcatcc gcttacagac aagctgtgac cgtctccggg agctgcatgt
 841 gtcagaggtt ttcaccgtca tcaccgaaac gcgcgagacg aaagggcctc gtgatacgcc
 901 tatttttata ggttaatgtc atgataataa tggtttctta gacgtcaggt ggcacttttc
 961 ggggaaatgt gcgcggaacc cctatttgtt tatttttcta aatacattca aatatgtatc
1021 cgctcatgag acaataaccc tgataaatgc ttcaataata ttgaaaaagg aagagtatga
1081 gtattcaaca tttccgtgtc gcccttattc ccttttttgc ggcattttgc cttcctgttt
1141 ttgctcaccc agaaacgctg gtgaaagtaa aagatgctga agatcagttg ggtgcacgag
1201 tgggttacat cgaactggat ctcaacagcg gtaagatcct tgagagtttt cgccccgaag
1261 aacgttttcc aatgatgagc acttttaaag ttctgctatg tggcgcggta ttatcccgta
1321 ttgacgccgg gcaagagcaa ctcggtcgcc gcatacacta ttctcagaat gacttggttg
1381 agtactcacc agtcacagaa aagcatctta cggatggcat gacagtaaga gaattatgca
1441 gtgctgccat aaccatgagt gataacactg cggccaactt acttctgaca acgatcggag
1501 gaccgaagga gctaaccgct tttttgcaca acatggggga tcatgtaact cgccttgatc
1561 gttgggaacc ggagctgaat gaagccatac caaacgacga gcgtgacacc acgatgcctg
1621 tagcaatggc aacaacgttg cgcaaactat taactggcga actacttact ctagcttccc
1681 ggcaacaatt aatagactgg atggaggcgg ataaagttgc aggaccactt ctgcgctcgg
1741 cccttccggc tggctggttt attgctgata aatctggagc cggtgagcgt gggtctcgcg
1801 gtatcattgc agcactgggg ccagatggta agccctcccg tatcgtagtt atctacacga
```

-continued

```
1861 cggggagtca ggcaactatg gatgaacgaa atagacagat cgctgagata ggtgcctcac
1921 tgattaagca ttggtaactg tcagaccaag tttactcata tatactttag attgatttaa
1981 aacttcattt ttaatttaaa aggatctagg tgaagatcct ttttgataat ctcatgacca
2041 aaatccctta acgtgagttt tcgttccact gagcgtcaga ccccgtagaa agatcaaag
2101 gatcttcttg agatcctttt tttctgcgcg taatctgctg cttgcaaaca aaaaaaccac
2161 cgctaccagc ggtggtttgt ttgccggatc aagagctacc aactctttt ccgaaggtaa
2221 ctggcttcag cagagcgcag ataccaaata ctgtccttct agtgtagccg tagttaggcc
2281 accacttcaa gaactctgta gcaccgccta catacctcgc tctgctaatc ctgttaccag
2341 tggctgctgc cagtggcgat aagtcgtgtc ttaccgggtt ggactcaaga cgatagttac
2401 cggataaggc gcagcggtcg ggctgaacgg ggggttcgtg cacacagccc agcttggagc
2461 gaacgaccta caccgaactg agatacctac agcgtgagct atgagaaagc gccacgcttc
2521 ccgaagggag aaaggcggac aggtatccgg taagcggcag ggtcggaaca ggagagcgca
2581 cgagggagct tccaggggga aacgcctggt atctttatag tcctgtcggg tttcgccacc
2641 tctgacttga gcgtcgattt ttgtgatgct cgtcagggg gcggagccta tggaaaaacg
2701 ccagcaacgc ggcctttta cggttcctgg ccttttgctg gccttttgct cacatgttct
2761 ttcctgcgtt atcccctgat tctgtggata accgtattac cgcctttgag tgagctgata
2821 ccgctcgccg cagccgaacg accgagcgca gcgagtcagt gagcgaggaa gcggaagagc
2881 gcccaatacg caaaccgcct ctccccgcgc gttggccgat tcattaatgc agctggcacg
2941 acaggtttcc cgactggaaa gcgggcagtg agcgcaacgc aattaatgtg agttagctca
3001 ctcattaggc accccaggct ttacacttta tgcttccggc tcgtatgttg tgtggaattg
3061 tgagcggata acaatttcac acaggaaaca gctatgacca tgattacgcc aagcttcgga
3121 tttggagcca agtctcataa acgccattgt ggaagaaagt cttgagttgg tggtaatgta
3181 acagagtagt aagaacagag aagagagaga gtgtgagata catgaattgt cgggcaacaa
3241 aaatcctgaa catcttattt tagcaaagag aaagagttcc gagtctgtag cagaagagtg
3301 aggagaaatt taagctcttg gacttgtgaa ttgttccgcc tcttgaatac ttcttcaatc
3361 ctcatatatt cttcttctat gttacctgaa aaccggcatt taatctcgcg ggtttattcc
3421 ggttcaacat tttttttgtt ttgagttatt atctgggctt aataacgcag gcctgaaata
3481 aattcaaggc ccaactgttt ttttttttaa gaagttgctg ttaaaaaaaa aaaagggaa
3541 ttaacaacaa caacaaaaaa agataaagaa ataataaca attactttaa ttgtagacta
3601 aaaaaacata gattttatca tgaaaaaag agaaagaaa taaaaacttg gatcaaaaaa
3661 aaaaacatac agatcttcta attattaact tttcttaaaa attaggtcct ttttcccaac
3721 aattaggttt agagttttgg aattaaacca aaagattgt tctaaaaaat actcaaattt
3781 ggtagataag tttccttatt ttaattagtc aatggtagat acttttttt cttttcttta
3841 ttagagtaga ttagaatctt ttatgccaag tattgataaa ttaaatcaag aagataaact
3901 atcataatca acatgaaatt aaaagaaaaa tctcatatat agtattagta ttctctatat
3961 atattatgat tgcttattct taatgggttg ggttaaccaa gacatagtct taatggaaag
4021 aatctttttt gaacttttc cttattgatt aaattcttct atagaaaaga aagaaattat
4081 ttgaggaaaa gtatatacaa aaagaaaaat agaaaaatgt cagtgaagca gatgtaatgg
4141 atgacctaat ccaaccacca ccataggatg tttctacttg agtcggtctt ttaaaaacgc
4201 acggtggaaa atatgacacg tatcatatga ttccttcctt tagtttcgtg ataataatcc
```

-continued

```
4261 tcaactgata tcttcctttt tttgttttgg ctaaagatat tttattctca ttaatagaaa 4321 agacggtttt gggcttttgg tttgcgatat aaagaagacc ttcgtgtgga agataataat 4381 tcatcctttc gtcttttcct gactcttcaa tctctcccaa agcctaaagc gatctctgca 4441 aatctctcgc gactctctct ttcaaggtat attttctgat tcttttgtt tttgattcgt 4501 atctgatctc caattttgt tatgtggatt attgaatctt ttgtataaat tgcttttgac 4561 aatattgttc gtttcgtcaa tccagcttct aaattttgtc ctgattacta agatatcgat 4621 tcgtagtgtt tacatctgtg taatttcttg cttgattgtg aaattaggat tttcaaggac 4681 gatctattca attttgtgt tttctttgtt cgattctctc tgttttaggt ttcttatgtt 4741 tagatccgtt tctctttggt gttgtttga tttctcttac ggcttttgat ttggtatatg 4801 ttcgctgatt ggtttctact tgttctattg ttttatttca gatgcagatc cccgggctca 4861 ctgtgcggtc tctaattctt tccatacttt tcttgctccg gttttcgcgc ggaatggagg 4921 aacggtcgcc ggcgccgaat tggtgcaagt aaagtatgga tagaatcgga ggccgcggtg 4981 aacgcggccg cttgctaccg agctcgaatt tccccgatcg ttcaaacatt tggcaataaa 5041 gtttcttaag attgaatcct gttgccggtc ttgcgatgat tatcatataa tttctgttga 5101 attacgttaa gcatgtaata attaacatgt aatgcatgac gttatttatg agatgggttt 5161 ttatgattag agtcccgcaa ttatacattt aatacgcgcg agaaaacaaa atatagcgcg 5221 caaactagga taaattatcg cgcgcggtgt catctatgtt actagatcgg
```

```
Construct #2
LOCUS           PHP35697 5270 bp DNA circular

DEFINITION      UBI3 PRO; gmir 168c-iag1c.pk007.b12; NOS term.

SOURCE
  ORGANISM

COMMENT         Component Fragments
                #1: FRAGMENT of PHP17474
                  parent position: from 6394 to 4240 original length: 4853 molecule position: from 1 to 4853

Left Terminus
                      EcoRI site #1

Right Terminus
                      SmaI site #1

#2: FRAGMENT of gmir 168c-iag1c.pk007.b12 with R.Sites
                  parent position: from 4 to 420 original length: 417 molecule position: from 4854 to 5270

Left Terminus
                      SmaI site #1

Right Terminus
                      EcoRI site #1

COMMENT         This file is created by Vector NTI

COMMENT         ORIGDB|GenBank

COMMENT         VNTDATE|472663677|

COMMENT         VNTDBDATE|473182320|

COMMENT         LSOWNER|
```

-continued

```
COMMENT          VNTNAME|PHP35697|

COMMENT          VNTAUTHORNAME|Mani Muthalagi|

COMMENT          VNTAUTHORTEL|5-1975|

COMMENT          VNTAUTHOREML

FEATURES                  Location/Qualifiers

CDS                  1077 . . . 1937

/vntifkey="4"

/label=AMP promoter             3111 . . . 4466

/vntifkey="30"

/label=UBQ3\PRO

/note="UBQ3 promoter isolated from Arabidopsis."

intron               4467 . . . 4841

/vntifkey="15"

/label=UBQ3\INTRON

/note="The first intron at 5'-end of gene"

misc_RNA             4877 . . . 4897

/vntifkey="53"

/label=AG-MTIF

/note="Synthetic sequence complementary to
translation initiation factor fron Aphis glycines. This is an
artificial microRNA."

misc_RNA             complement(4944 . . . 4964)

/vntifkey="53"

/label=AG-MTIF\STAR\SEQ

/note="Synthetic sequence complimentary to
sequence AG-MTIF to silence the expression of translation initiation
factor in Aphis glycines. This sequence forms the hairpin in an
artificial microRNA precursor"

terminator           4992 . . . 5269

/vntifkey="43"

/label=NOS\TERM misc_RNA             4898 . . . 4943

/vntifkey="53"

/label=GM\MIRNA\PRECURSOR\168C

BASE COUNT       1422 a 1127 c 1149 g 1572 t

ORIGIN                                                     (SEQ ID NO: 93)
   1 aattcactgg ccgtcgtttt acaacgtcgt gactgggaaa accctggcgt tacccaactt 61 aatcgccttg cagcacatcc ccctttcgcc agctggcgta atagcgaaga ggcccgcacc 121 gatcgccctt cccaacagtt gcgcagcctg aatggcgaat ggcgcctgat gcggtatttt 181 ctccttacgc atctgtgcgg tatttcacac cgcatacgtc aaagcaacca tagtacgcgc 241 cctgtagcgg cgcattaagc gcggcgggtg tggtggttac gcgcagcgtg accgctacac 301 ttgccagcgc cctagcgccc gctcctttcg ctttcttccc ttcctttctc gccacgttcg
```

-continued

```
 361 ccggctttcc ccgtcaagct ctaaatcggg ggctcccttt agggttccga tttagtgctt 421 tacggcacct cgaccccaaa aaacttgatt tgggtgatgg ttcacgtagt gggccatcgc 481 cctgatagac ggttttttcgc cctttgacgt tggagtccac gttctttaat agtggactct 541 tgttccaaac tggaacaaca ctcaaccccta tctcgggcta ttcttttgat ttataaggga 601 ttttgccgat tcggcctat tggttaaaaa atgagctgat ttaacaaaaa tttaacgcga 661 attttaacaa atattaacg tttacaattt tatggtgcac tctcagtaca atctgctctg 721 atgccgcata gttaagccag ccccgacacc cgccaacacc cgctgacgcg ccctgacggg 781 cttgtctgct cccggcatcc gcttacagac aagctgtgac cgtctccggg agctgcatgt 841 gtcagaggtt ttcaccgtca tcaccgaaac gcgcgagacg aaagggcctc gtgatacgcc 901 tatttttata ggttaatgtc atgataataa tggtttctta cacgtcaggt ggcacttttc 961 ggggaaatgt gcgcggaacc cctatttgtt tatttttcta aatacattca aatatgtatc 1021 cgctcatgag acaataaccc tgataaatgc ttcaataata ttgaaaaagg aagagtatga 1081 gtattcaaca tttccgtgtc gcccttattc ccttttttgc ggcattttgc cttcctgttt 1141 ttgctcaccc agaaacgctg gtgaaagtaa aagatgctga agatcagttg ggtgcacgag 1201 tgggttacat cgaactggat ctcaacagcg gtaagatcct tgagagtttt cgccccgaag 1261 aacgttttcc aatgatgagc acttttaaag ttctgctatg tggcgcggta ttatcccgta 1321 ttgacgccgg gcaagagcaa ctcggtcgcc gcatacacta ttctcagaat gacttggttg 1381 agtactcacc agtcacagaa aagcatctta cggatggcat gacagtaaga gaattatgca 1441 gtgctgccat aaccatgagt gataacactg cggccaactt acttctgaca acgatcggag 1501 gaccgaagga gctaaccgct ttttgcaca acatggggga tcatgtaact cgccttgatc 1561 gttgggaacc ggagctgaat gaagccatac caaacgacga gcgtgacacc acgatgcctg 1621 tagcaatggc aacaacgttg cgcaaactat taactggcga actacttact ctagcttccc 1681 ggcaacaatt aatagactgg atggaggcgg ataaagttgc aggaccactt ctgcgctcgg 1741 cccttccggc tggctggttt attgctgata atctggagc cggtgagcgt gggtctcgcg 1801 gtatcattgc agcactgggg ccagatggta agccctcccg tatcgtagtt atctacacga 1861 cggggagtca ggcaactatg gatgaacgaa atagacagat cgctgagata ggtgcctcac 1921 tgattaagca ttggtaactg tcagaccaag tttactcata tatactttag attgatttaa 1981 aacttcattt ttaatttaaa aggatctagg tgaagatcct ttttgataat ctcatgacca 2041 aaatccctta acgtgagttt tcgttccact gagcgtcaga ccccgtagaa aagatcaaag 2101 gatcttcttg agatcctttt tttctgcgcg taatctgctg cttgcaaaca aaaaaaccac 2161 cgctaccagc ggtggtttgt ttgccggatc aagagctacc aactctttt ccgaaggtaa 2221 ctggcttcag cagagcgcag ataccaaata ctgtccttct agtgtagccg tagttaggcc 2281 accacttcaa gaactctgta gcaccgccta catacctcgc tctgctaatc ctgttaccag 2341 tggctgctgc cagtggcgat aagtcgtgtc ttaccgggtt ggactcaaga cgatagttac 2401 cggataaggc gcagcggtcg ggctgaacgg ggggttcgtg cacacagccc agcttggagc 2461 gaacgaccta caccgaactg agatacctac agcgtgagct atgagaaagc gccacgcttc 2521 ccgaagggag aaaggcggac aggtatccgg taagcggcag ggtcggaaca ggagagcgca 2581 cgagggagct tccaggggga aacgcctggt atctttatag tcctgtcggg tttcgccacc 2641 tctgacttga gcgtcgattt ttgtgatgct cgtcaggggg gcggagccta tggaaaaacg 2701 ccagcaacgg ggccttttta cggttcctgg cctttttgctg gccttttgct cacatgttct 2761 ttcctgcgtt atcccctgat tctgtggata accgtattac cgcctttgag tgagctgata
```

-continued

```
2821 ccgctcgccg cagccgaacg accgagcgca gcgagtcagt gagcgaggaa gcggaagagc
2881 gcccaatacg caaaccgcct ctccccgcgc gttggccgat tcattaatgc agctggcacg
2941 acaggtttcc cgactggaaa gcgggcagtg agcgcaacgc aattaatgtg agttagctca
3001 ctcattaggc accccaggct ttacacttta tgcttccggc tcgtatgttg tgtggaattg
3061 tgagcggata caatttcac acaggaaaca gctatgacca tgattacgcc aagcttcgga
3121 tttggagcca agtctcataa acgccattgt ggaagaaagt cttgagttgg tggtaatgta
3181 acagagtagt aagaacagag aagagagaga gtgtgagata catgaattgt cgggcaacaa
3241 aaatcctgaa catcttattt tagcaaagag aaagagttcc gagtctgtag cagaagagtg
3301 aggagaaatt taagctcttg gacttgtgaa ttgttccgcc tcttgaatac ttcttcaatc
3361 ctcatatatt cttcttctat gttacctgaa aaccggcatt taatctcgcg ggtttattcc
3421 ggttcaacat ttttttgtt ttgagttatt atctgggctt aataacgcag gcctgaaata
3481 aattcaaggc ccaactgttt ttttttttaa gaagttgctg ttaaaaaaaa aaaaagggaa
3541 ttaacaacaa caacaaaaaa agataaagaa aataataaca attactttaa ttgtagacta
3601 aaaaaacata gattttatca tgaaaaaaag agaaagaaa taaaaacttg gatcaaaaaa
3661 aaaaacatac agatcttcta attattaact tttcttaaaa attaggtcct ttttcccaac
3721 aattaggttt agagttttgg aattaaacca aaaagattgt tctaaaaaat actcaaattt
3781 ggtagataag tttccttatt ttaattagtc aatggtagat actttttttt cttttcttta
3841 ttagagtaga ttagaatctt ttatgccaag tattgataaa ttaaatcaag aagataaact
3901 atcataatca acatgaaatt aaaagaaaaa tctcatatat agtattagta ttctctatat
3961 atattatgat tgcttattct taatgggttg ggttaaccaa gacatagtct taatggaaag
4021 aatcttttt gaacttttc cttattgatt aaattcttct atagaaaaga aagaaattat
4081 ttgaggaaaa gtatatacaa aaagaaaaat agaaaaatgt cagtgaagca gatgtaatgg
4141 atgacctaat ccaaccacca ccataggatg tttctacttg agtcggtctt ttaaaaacgc
4201 acggtggaaa atatgacacg tatcatatga ttccttcctt tagtttcgtg ataataatcc
4261 tcaactgata tcttccttt tttgttttgg ctaaagatat tttattctca ttaatagaaa
4321 agacggtttt gggcttttgg tttgcgatat aaagaagacc ttcgtgtgga agataataat
4381 tcatcctttc gtctttttct gactcttcaa tctctcccaa agcctaaagc gatctctgca
4441 aatctctcgc gactctctct ttcaaggtat attttctgat tcttttgtt tttgattcgt
4501 atctgatctc caatttttgt tatgtggatt attgaatctt ttgtataaat tgcttttgac
4561 aatattgttc gtttcgtcaa tccagcttct aaattttgtc ctgattacta agatatcgat
4621 tcgtagtgtt tacatctgtg taatttcttg cttgattgtg aaattaggat tttcaaggac
4681 gatctattca attttgtgt tttctttgtt cgattctctc tgttttaggt ttcttatgtt
4741 tagatccgtt tctctttggt gttgtttga tttctcttac ggcttttgat ttggtatatg
4801 ttcgctgatt ggtttctact tgttctattg ttttatttca gatgcagatc cccgggctca
4861 ctgtgcggtc tctaattata cttcaaaatt acatcggccg gttttcgcgc ggaatggagg
4921 aacggtcgcc ggcgccgaat tgggcgatga aattttgaag aataatcgga ggccgcggtg
4981 aacgcggccg cttgctaccg agctcgaatt ccccgatcg ttcaaacatt tggcaataaa
5041 gtttcttaag attgaatcct gttgccggtc ttgcgatgat tatcatataa tttctgttga
5101 attacgttaa gcatgtaata attaacatgt aatgcatgac gttatttatg agatgggttt
5161 ttatgattag agtcccgcaa ttatacattt aatacgcgat agaaaacaaa atatagcgcg
```

-continued 5221 caaactagga taaattatcg cgcgcggtgt catctatgtt actagatcgg

```
Construct #3
LOCUS           PHP35698 5270 bp DNA circular

DEFINITION      UBI3 PRoO gmir168c-iag1c.pk001.c6. miRNA construct of AG-
                TIK for SOY.

SOURCE
  ORGANISM

COMMENT         Component Fragments
                #1: FRAGMENT of PHP17474
                  parent position: from 6394 to 4240 original length: 4853 molecule position: from 1 to 4853

Left Terminus
                      EcoRI site #1

Right Terminus
                      SmaI site #1

#2: FRAGMENT of gmir168c-iag1c.pk001.c6 with R.Sites
                  parent position: from 4 to 420 original length: 417 molecule position: from 4854 to 5270

Left Terminus
                      SmaI site #1

Right Terminus
                      EcoRI site #1

COMMENT         This file is created by Vector NTI

COMMENT         ORIGDB|GenBank

COMMENT         VNTDATE|472663281|

COMMENT         VNTDBDATE|473182342|

COMMENT         LSOWNER|

COMMENT         VNTNAME|PHP35698|

COMMENT         VNTAUTHORNAME|Mani Muthalagi|

COMMENT         VNTAUTHORTEL|5-1975|

COMMENT         VNTAUTHOREML

COMMENT         VNTREPLTYPE|Plasmid

COMMENT         VNTEXTCHREPL|Bacteria

FEATURES          Location/Qualifiers
    CDS           1077 . . . 1937

/vntifkey="4"

/label=AMP promoter      3111 . . . 4466

/vntifkey="30"

/label=UBQ3\PRO

/note="UBQ3 promoter isolated from Arabidopsis."

intron        4467 . . . 4841
```

-continued

/vntifkey="15"

/label=UBQ3\INTRON

/note="The first intron at 5'-end of gene"

terminator 4992 . . . 5269

/vntifkey="43"

/label=NOS\TERM misc_RNA 4877 . . . 4897

/vntifkey="53"

/label=AG-MTIK

/note="Synthetic sequence complementary to tousled like kinase fron Aphis glycines. This is an artificial microRNA"

misc_RNA complement(4944 . . . 4964)

/vntifkey="53"

/label=AG-MTIK\STAR\SEQ

/note="Synthetic sequence complimentary to sequence AG-MTIK to silence the expression of tousled like kinase in Aphis glycines. This sequence forms the hairpin in an artificial microRNA precursor"

misc_RNA 4898 . . . 4943

/vntifkey="53"

/label=GM\MIRNA\PRECURSOR\168C

BASE COUNT 1417 a 1132 c 1150 g 1571 t

ORIGIN (SEQ ID NO: 94)

```
   1 aattcactgg ccgtcgtttt acaacgtcgt gactgggaaa accctggcgt tacccaactt
  61 aatcgccttg cagcacatcc ccctttcgcc agctggcgta atagcgaaga ggcccgcacc
 121 gatcgccctt cccaacagtt gcgcagcctg aatggcgaat ggcgcctgat gcggtatttt
 181 ctccttacgc atctgtgcgg tatttcacac cgcatacgtc aaagcaacca tagtacgcgc
 241 cctgtagcgg cgcattaagc gcggcgggtg tggtggttac gcgcagcgtg accgctacac
 301 ttgccagcgc cctagcgccc gctcctttcg ctttcttccc ttcctttctc gccacgttcg
 361 ccggctttcc ccgtcaagct ctaaatcggg ggctcccttt agggttccga tttagtgctt
 421 tacggcacct cgaccccaaa aaacttgatt tgggtgatgg ttcacgtagt gggccatcgc
 481 cctgatagac ggtttttcgc cctttgacgt tggagtccac gttctttaat agtggactct
 541 tgttccaaac tggaacaaca ctcaacccta tctcgggcta ttcttttgat ttataaggga
 601 ttttgccgat ttcggcctat tggttaaaaa atgagctgat ttaacaaaaa tttaacgcga
 661 attttaacaa aatattaacg tttacaattt tatggtgcac tctcagtaca atctgctctg
 721 atgccgcata gttaagccag ccccgacacc cgccaacacc cgctgacgcg ccctgacggg
 781 cttgtctgct cccggcatcc gcttacagac aagctgtgac cgtctccggg agctgcatgt
 841 gtcagaggtt ttcaccgtca tcaccgaaac gcgcgagacg aaagggcctc gtgatacgcc
 901 tatttttata ggttaatgtc atgataataa tggtttctta gacgtcaggt ggcacttttc
 961 ggggaaatgt gcgcggaacc cctatttgtt tatttttcta aatacattca aatatgtatc
1021 cgctcatgag acaataaccc tgataaatgc ttcaataata ttgaaaaagg aagagtatga
1081 gtattcaaca tttccgtgtc gcccttattc ccttttttgc ggcattttgc cttcctgttt
1141 ttgctcaccc agaaacgctg gtgaaagtaa aagatgctga agatcagttg ggtgcacgag
```

-continued

```
1201 tgggttacat cgaactggat ctcaacagcg gtaagatcct tgagagtttt cgccccgaag 1261 aacgttttcc aatgatgagc acttttaaag ttctgctatg tggcgcggta ttatcccgta 1321 ttgacgccgg gcaagagcaa ctcggtcgcc gcatacacta ttctcagaat gacttggttg 1381 agtactcacc agtcacagaa aagcatctta cggatggcat gacagtaaga gaattatgca 1441 gtgctgccat aaccatgagt gataacactg cggccaactt acttctgaca acgatcggag 1501 gaccgaagga gctaaccgct tttttgcaca acatggggga tcatgtaact cgccttgatc 1561 gttgggaacc ggagctgaat gaagccatac caaacgacga gcgtgacacc acgatgcctg 1621 tagcaatggc aacaacgttg cgcaaactat taactggcga actacttact ctagcttccc 1681 ggcaacaatt aatagactgg atggaggcgg ataaagttgc aggaccactt ctgcgctcgg 1741 cccttccggc tggctggttt attgctgata aatctggagc cggtgagcgt gggtctcgcg 1801 gtatcattgc agcactgggg ccagatggta agccctcccg tatcgtagtt atctacacga 1861 cggggagtca ggcaactatg gatgaacgaa atagacagat cgctgagata ggtgcctcac 1921 tgattaagca ttggtaactg tcagaccaag tttactcata tatactttag attgatttaa 1981 aacttcattt ttaatttaaa aggatctagg tgaagatcct ttttgataat ctcatgacca 2041 aaatccctta acgtgagttt tcgttccact gagcgtcaga ccccgtagaa aagatcaaag 2101 gatcttcttg agatcctttt tttctgcgcg taatctgctg cttgcaaaca aaaaaaccac 2161 cgctaccagc ggtggtttgt ttgccggatc aagagctacc aactctttt ccgaaggtaa 2221 ctggcttcag cagagcgcag ataccaaata ctgtccttct agtgtagccg tagttaggcc 2281 accacttcaa gaactctgta gcaccgccta catacctcgc tctgctaatc ctgttaccag 2341 tggctgctgc cagtggcgat aagtcgtgtc ttaccgggtt ggactcaaga cgatagttac 2401 cggataaggc gcagcggtcg ggctgaacgg ggggttcgtg cacacagccc agcttggagc 2461 gaacgaccta caccgaactg agatacctac agcgtgagct atgagaaagc gccacgcttc 2521 ccgaagggag aaaggcggac aggtatccgg taagcggcag ggtcggaaca ggagagcgca 2581 cgagggagct tccaggggga aacgcctggt atctttatag tcctgtcggg tttcgccacc 2641 tctgacttga gcgtcgattt tgtgatgct cgtcaggggg gcggagccta tggaaaaacg 2701 ccagcaacgc ggccttttta cggttcctgg ccttttgctg gccttttgct cacatgttct 2761 ttcctgcgtt atcccctgat tctgtggata accgtattac cgcctttgag tgagctgata 2821 ccgctcgccg cagccgaacg accgagcgca gcgagtcagt gagcgaggaa gcggaagagc 2881 gcccaatacg caaaccgcct ctccccgcgc gttggccgat tcattaatgc agctggcacg 2941 acaggtttcc cgactggaaa gcgggcagtg agcgcaacgc aattaatgtg agttagctca 3001 ctcattaggc accccaggct ttacacttta tgcttccggc tcgtatgttg tgtggaattg 3061 tgagcggata acaatttcac acaggaaaca gctatgacca tgattacgcc aagcttcgga 3121 tttggagcca agtctcataa acgccattgt ggaagaaagt cttgagttgg tggtaatgta 3181 acagagtagt aagaacagag aagagagaga gtgtgagata catgaattgt cgggcaacaa 3241 aaatcctgaa catcttattt tagcaaagag aaagagttcc gagtctgtag cagaagagtg 3301 aggagaaatt taagctcttg gacttgtgaa ttgttccgcc tcttgaatac ttcttcaatc 3361 ctcatatatt cttcttctat gttacctgaa aaccggcatt taatctcgcg ggtttattcc 3421 ggttcaacat ttttttttgtt ttgagttatt atctgggctt aataacgcag gcctgaaata 3481 aattcaaggc ccaactgttt tttttttttaa gaagttgctg ttaaaaaaaa aaaagggaa 3541 ttaacaacaa caacaaaaaa agataaagaa aataataaca attactttaa ttgtagacta 3601 aaaaaacata gattttatca tgaaaaaaag agaaaagaaa taaaaacttg gatcaaaaaa
```

```
3661 aaaaacatac agatcttcta attattaact tttcttaaaa attaggtcct ttttcccaac 3721 aattaggttt agagttttgg aattaaacca aaaagattgt tctaaaaaat actcaaattt 3781 ggtagataag tttccttatt ttaattagtc aatggtagat actttttttt cttttctttta 3841 ttagagtaga ttagaatctt ttatgccaag tattgataaa ttaaatcaag aagataaact 3901 atcataatca acatgaaatt aaaagaaaaa tctcatatat agtattagta ttctctatat 3961 atattatgat tgcttattct taatgggttg ggttaaccaa gacatagtct taatggaaag 4021 aatctttttt gaactttttc cttattgatt aaattcttct atagaaaaga aagaaattat 4081 ttgaggaaaa gtatatacaa aaagaaaaat agaaaaatgt cagtgaagca gatgtaatgg 4141 atgacctaat ccaaccacca ccataggatg tttctacttg agtcggtctt ttaaaaacgc 4201 acggtggaaa atatgacacg tatcatatga ttccttcctt tagtttcgtg ataataatcc 4261 tcaactgata tcttcctttt tttgttttgg ctaaagatat tttattctca ttaatagaaa 4321 agacggtttt gggcttttgg tttgcgatat aaagaagacc ttcgtgtgga agataataat 4381 tcatcctttc gtcttttttct gactcttcaa tctctcccaa agcctaaagc gatctctgca 4441 aatctctcgc gactctctct ttcaaggtat atttttctgat tctttttgtt tttgattcgt 4501 atctgatctc caattttttgt tatgtggatt attgaatctt ttgtataaat tgcttttgac 4561 aatattgttc gtttcgtcaa tccagcttct aaattttgtc ctgattacta agatatcgat 4621 tcgtagtgtt tacatctgtg taatttcttg cttgattgtg aaattaggat tttcaaggac 4681 gatctattca attttttgtgt tttctttgtt cgattctctc tgtttttaggt ttcttatgtt 4741 tagatccgtt tctctttggt gttgttttga tttctcttac ggcttttgat ttggtatatg 4801 ttcgctgatt ggtttctact tgttctattg ttttatttca gatgcagatc cccgggctca 4861 ctgtgcggtc tctaatttct tcaccacttc aatgcacccg gttttcgcgc ggaatggagg 4921 aacggtcgcc ggcgccgaat tggctgcata gaagtggtga tgaaatcgga ggccgcggtg 4981 aacgcggccg cttgctaccg agctcgaatt tccccgatcg ttcaaacatt tggcaataaa 5041 gtttcttaag attgaatcct gttgccggtc ttgcgatgat tatcatataa tttctgttga 5101 attacgttaa gcatgtaata attaacatgt aatgcatgac gttatttatg agatgggttt 5161 ttatgattag agtcccgcaa ttatacattt aatacgcgat agaaaacaaa atatagcgcg 5221 caaactagga taaattatcg cgcgcggtgt catctatgtt actagatcgg
```

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A plant cell having stably incorporated into its genome a heterologous polynucleotide comprising a silencing element, wherein said silencing element, when ingested by a pest, reduces the level of a target sequence comprising SEQ ID NO:11 in said pest, wherein said pest is from the family Aphididae and said silencing element comprises
a polynucleotide comprising a nucleotide sequence having at least 95% sequence identity to SEQ ID NO: 12 and a nucleotide sequence having at least 95% sequence identity to SEQ ID NO: 13.

2. The plant cell of claim 1, wherein said pest comprises Aphis glycines.

3. The plant cell of claim 1, wherein the reduction of the level of target pest sequence controls the pest from the family Aphididae.

4. The plant cell of claim 1, wherein said silencing element comprises a hairpin RNA.

5. A plant cell having stably incorporated into its genome a heterologous polynucleotide comprising a silencing element, wherein said silencing element, when ingested by a pest, reduces the level of a target sequence comprising SEQ ID NO:11 in said pest, wherein said pest is from the family Aphididae and said silencing element comprises, in the following order, a first segment, a second segment, and a third segment, wherein
a) said first segment comprises 95% sequence identity to SEQ ID NO: 12 or 95% sequence identity to SEQ ID NO: 13;
b) said second segment comprises a loop of sufficient length to allow the silencing element to be transcribed as a hairpin RNA; and,
c) said third segment comprises a nucleotide sequence having at least 93% complementary to the first segment.

6. The plant cell of claim 1, wherein said silencing element is operably linked to a heterologous promoter.

7. The plant cell of claim 1, wherein said plant cell has stably incorporated into its genome a second polynucleotide comprising a suppressor enhancer element comprising the target pest sequence or an active variant or fragment thereof, wherein the combined expression of the silencing element and the suppressor enhancer element increases the concentration of an inhibitory RNA specific for the pest target sequence in said plant cell.

8. The plant cell of claim 1, wherein said plant cell is from a monocot.

9. The plant cell of claim 8, wherein said monocot is maize, barley, millet, wheat or rice.

10. The plant cell of claim 1, wherein said plant is from a dicot.

11. The plant cell of claim 10, wherein said plant cell is from soybean, canola, alfalfa, sunflower, safflower, tobacco, Arabidopsis, or cotton.

12. A plant or plant part comprising the plant cell of claim 1.

13. The plant or plant part comprising the plant cell of claim 7, wherein the combined expression of said silencing element and the suppressor enhancer element increases the concentration of an inhibitory RNA specific for the pest target sequence in the phloem of said plant or plant part.

14. A transgenic seed from the plant of claim 12, wherein the transgenic seed comprises the heterologous polynucleotide comprising the silencing element.

15. A method for controlling Aphididae comprising feeding to a Aphididae a composition comprising a silencing element, wherein said silencing element, when ingested by said Aphididae, reduces the level of a target Aphididae sequence comprising SEQ ID NO:11 and thereby controls the Aphididae, wherein the silencing element comprises
a) a polynucleotide comprising the sequences set forth in SEQ ID NO:12 and 13; or
b) a polynucleotide comprising a nucleotide sequence having at least 95% sequence identity to SEQ ID NO: 12 and a nucleotide sequence having at least 95% sequence identity to SEQ ID NO: 13.

16. The method of claim 15, wherein said composition comprises a plant or plant part having stably incorporated into its genome a polynucleotide comprising said silencing element.

17. The method of claim 15, wherein said pest comprises Aphis glycines.

18. A method for controlling Aphididae comprising feeding to a Aphididae a composition comprising a silencing element, wherein said silencing element, when ingested by said Aphididae, reduces the level of a target Aphididae sequence comprising SEQ ID NO:11 and thereby controls the Aphididae, wherein said polynucleotide comprising the silencing element comprises, in the following order, a first segment, a second segment, and a third segment, wherein
a) said first segment comprises 95% sequence identity to SEQ ID NO: 12 or 95% sequence identity to SEQ ID NO: 13;

b) said second segment comprises a loop of sufficient length to allow the silencing element to be transcribed as a hairpin RNA; and, c) said third segment having at least 95% complementary to the first segment.

19. The method of claim 15, wherein said silencing element is operably linked to a heterologous promoter.

20. The method of claim 16, wherein said plant or plant part has stably incorporated into its genome a second polynucleotide comprising a suppressor enhancer element comprising the target pest sequence or an active variant or fragment thereof, wherein the combined expression of the silencing element and the suppressor enhancer element increases the concentration of an inhibitory RNAi specific for the pest target sequence in said plant cell.

21. The method of claim 20, wherein the combined expression of said silencing element and the suppressor enhancer element increases the concentration of an inhibitory RNA specific for the pest target sequence in the phloem of said plant or plant part.

22. The method of claim 16, wherein said plant is a monocot.

23. The method of claim 22, wherein said monocot is maize, barley, millet, wheat or rice.

24. The method of claim 16, wherein said plant is a dicot.

25. The method of claim 24, wherein said plant is soybean, canola, alfalfa, sunflower, safflower, tobacco, Arabidopsis, or cotton.

26. The plant cell of claim 1, wherein the silencing element comprises a polynucleotide comprising the sequences set forth in SEQ ID NOS: 12 and 13.

27. The plant cell of claim 26, wherein the reduction of the level of the target pest sequence controls the pest from the family Aphididae.

28. The plant cell of claim 26, wherein said silencing element comprises a hairpin RNA.

29. The plant cell of claim 5, wherein said polynucleotide comprising the silencing element comprises, in the following order, a first segment, a second segment, and a third segment, wherein a) said first segment comprises SEQ ID NO: 12 or SEQ ID NO: 13;

b) said second segment comprises a loop of sufficient length to allow the silencing element to be transcribed as a hairpin RNA; and, c) said third segment comprises a nucleotide sequence having at least 100% complementary to the first segment.

* * * * *

UNITED STATES PATENT AND TRADEMARK OFFICE
CERTIFICATE OF CORRECTION

PATENT NO. : 8,367,895 B2
APPLICATION NO. : 12/351189
DATED : February 5, 2013
INVENTOR(S) : Herrmann et al.

Page 1 of 1

It is certified that error appears in the above-identified patent and that said Letters Patent is hereby corrected as shown below:

In the Specification

Column 17, line 37, delete "*Bial.*" and insert --*Biol.*-- therefor.

Column 17, line 59, delete "Tomero" and insert --Tornero-- therefor.

Column 25, line 5, delete "cassaya" and insert --cassava-- therefor.

In the Claims

Column 111, line 55, delete "93%" and insert --95%-- therefor.

Signed and Sealed this
Seventh Day of May, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,367,895 B2 | Page 1 of 1 |
| APPLICATION NO. | : 12/351189 | |
| DATED | : February 5, 2013 | |
| INVENTOR(S) | : Herrmann et al. | |

It is certified that error appears in the above-identified patent and that said Letters Patent is hereby corrected as shown below:

In the Specification

Column 24, line 64, delete "*cereals*" and insert --*cereale*-- therefor.

Signed and Sealed this
Seventh Day of January, 2014

Margaret A. Focarino
*Commissioner for Patents of the United States Patent and Trademark Office*

SEQUENCE LISTING

<160> NUMBER OF SEQ ID NOS: 94

<210> SEQ ID NO 1
<211> LENGTH: 678
<212> TYPE: DNA
<213> ORGANISM: Aphis glycines
<220> FEATURE:
<221> NAME/KEY: misc_feature
<222> LOCATION: 644, 645, 646, 647, 656, 671, 672, 673, 674

<223> OTHER INFORMATION: n = A,T,C or G

<400> SEQUENCE: 1

```
tatttttatt ttgctcatag tccatagatt ttatttatca ttaatttagt ttaggtatat      60
tgtgtacata atataaatta tctgttttc tactacgacg cttcgttagg gactttgttg     120
gtaacgtagc tgtcttcact tttcgtcggc ccagacgcac agtgagaatc gaattgtggc    180
caacaataat tgttacgaca tcaaaacttt ttaccaatga acgacattaa gttgtgacac    240
tgatttactg tacatattac tattttaaaa gataatttca tcaaaaaatg tttctttggg    300
attgggttac tggcgttctg ggatatttag gactgtgaaa aaatcaggaa aacttctatt    360
ccttggttta gataatgctg gaaaaactac tttattacat atgttgaaag atgatcgttt    420
ggcacaacac actccaacat tacatccaac atctgaggaa ttgtctgttg aaacataaa     480
attcacaacg tttgatttgg gtggccattc acaagcaaga aaagtatgga aagattattt    540
ccctgctgta gatgcaattg tattttggt agacgcttgt gacaaatcta gaattatgga    600
aagtaaaaat gaattagatt cattattgct tgatgaatcc ttannnnact gccccntact    660
cgttcttggg nnnnaaat                                                   678
```

<210> SEQ ID NO 2
<211> LENGTH: 697
<212> TYPE: DNA
<213> ORGANISM: Aphis glycines
<220> FEATURE:
<221> NAME/KEY: misc_feature
<222> LOCATION: 496, 497, 610, 611, 659, 660, 661, 663, 664, 665, 670, 671, 672, 677, 678, 679, 682, 683, 684, 685, 686, 687, 688, 689, 690, 691, 692, 693, 694, 696, 697
<223> OTHER INFORMATION: n = A,T,C or G

<400> SEQUENCE: 2

```
cttatttatt ttattaaaaa atatgagccc tacagattaa aaattgtaat taaaaataag     60
caaagtaata ctattcttga tgttatgtat aattgagtac tggatgaagg tgttgatttt    120
attgctgtgt catctactgg aatacttgat gatgtcgaaa ttaggttgtc agtgagtaca    180
attgtggcac cgggacttag attcaaccat tctgtagttg atatcgagtt tccagaattg    240
aaattcgagt tttcggatcc aacaacaata gttaaagtat catgcaaatt tgatacttgg    300
tctgataaac gaacacgctg tgtatagttt gtatccatat tgatcattaa tgtgtagttc    360
tcatgtccat gcaaaaatct ggttaaaaca aacactgtat tattgttaag aacatcaatc    420
gccaaccctc cttttttaaa cgtttcagtc tggcgtaatt tcgatatgga tttgaaaaag    480
tttaaataac ttttannatt tttatttcc gtctgcacgt ttctcgtgac ataatctggg     540
tgtatcgcaa cccacggttc atgtgtgcta ttagtgaacc ctgcattttt cgtatcatcc    600
cactgcatan nacttcttgc ataattgatt ttatctgatg tatcttccat accaatttnn    660
ncnnnatatn nnctatnnnt annnnnnnnn nnnntnn                              697
```

<210> SEQ ID NO 3
<211> LENGTH: 587
<212> TYPE: DNA
<213> ORGANISM: Aphis glycines
<220> FEATURE:
<221> NAME/KEY: misc_feature
<222> LOCATION: 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 587
<223> OTHER INFORMATION: n = A,T,C or G

<400> SEQUENCE: 3

```
tggtgataag gaattacaat ctaacaatct tgctctcagc tatgtagcta agcaatttgt      60
gtttaccacc actgtaaatg ataataaatt atttggcggc tcggttttcc aaaaattatc     120
tgataaattg gatttgggct tgcaagtttc ttggtcatct gaaagcaatg attcttcact     180
tgctgtgggt tctcagtatc aactaaacca agacgttaag ttgcgcgcca agattaacaa     240
caagagtcaa ttgtgcatag gctctggcat taaagtcaaa gaaggtgtaa cattgacatt     300
ggccagctta ttggaatgtc gtcaattcaa ccaaggcggt cataaatttg gtattggctt     360
agaacttgct ttgtaagcaa tacacatgcc aaacttattt gtacgttatg tagacaaaat     420
gtattgtcag taaacgtagg attattaaac ataatcataa gagtattttt actacattaa     480
ataattcagt gtgtatttgt ttaaaattaa ttaggaaaaa tataatttat atcagttgct     540
ctcgttannn nnnnnnnnn nnnnnnnnnn nnnnnnnnnn nnnnnan                    587

<210> SEQ ID NO 4
<211> LENGTH: 465
<212> TYPE: DNA
<213> ORGANISM: Aphis glycines

<400> SEQUENCE: 4
cccacgcgtc cgaagttatt gtccttaacc acccaggtca agttggtgct ggttactcac      60
cagttcttga ctgtcacacc gcccacattg cttgtagatt ctcagagctc gttgagaaga     120
tcgacagacg taccggtaag accctcgaag cttcaccaaa gttcgtcaag tcaggtgatg     180
ctgccatcgt caagctcgtt ccaaccaagc caatgtgtgt tgagacttac aacgagtacc     240
caccactcgg tcgtttcgct gtccgtgaca tgcgtcaaac cgttgctgtt ggtgtcatca     300
agtctgttga agagactgaa aagggtggta agaccaccaa ggctgctgaa aaggcaggta     360
agaagaagta aactccaaac gttcagctat cttagttgcg cgctggtgca aaatttctct     420
ttgtctctca cgtgttaaaa atgaaatgca taagttctcc ttaat                    465

<210> SEQ ID NO 5
<211> LENGTH: 251
<212> TYPE: DNA
<213> ORGANISM: Aphis glycines
<220> FEATURE:
<221> NAME/KEY: misc_feature
<222> LOCATION: 211, 212, 213, 214, 218, 219, 220, 221, 222
<223> OTHER INFORMATION: n = A,T,C or G

<400> SEQUENCE: 5
cccacgcgtc cggatcgcag gcgcgaatac cagctcacag attctgctaa atattattta      60
atggaaatag acagagtggc cagtccaaat tatctgccca cagaacaaga catacttaga     120
gtaagggtac ccacgacggg cattatcgaa tacccgttcg atctagaaga aattcggttt     180
aggatggttg atgttggagg ccagagatca nnnngacnnn nntggattca ctgttttgag     240
aatgtaacat c                                                          251

<210> SEQ ID NO 6
<211> LENGTH: 604
<212> TYPE: DNA
<213> ORGANISM: Aphis glycines

<400> SEQUENCE: 6
acaaacgaag aactgaaaca ccaattaagc agtcaacaga aacaatcga acagcacaag       60 tcacacataa ataagtgcat tgaagtggtg aagaagctat tgaaagaaaa gtcaaatatt     120
gaaaaaaaag aagcaagaca gcggtgtatg caaaacagac ttcggcttgg ccagtttgta     180
```

```
acgcaaaggg ttggtgcaca atttcaagaa aattggactg atggctatgc gtttcaagaa    240
ttgtctagaa gacaagaaga aataacgtca gaaagagaag agattgaccg acagaaaaag    300
atgttggtca aaaaacggcc atcaaacagt gaaactggtg gacgcaaacg agctagtagt    360
cagtcgggta caggaagtag tagttcgagt actaacagtg taccaatcaa ttcgacgcct    420 tcagttttcta caccacctat aacgctaccc agtgcaagta tcaacaataa ccaagttact    480
ggtgctacaa caggcacggt cttgcacaac ggcactgtag ccccatcgtc cgccttggac    540
acagcaacgt tcctaaagcc agaagctgtt ccgggtttat cgtggcaaga gtattacgaa    600
gcag                                                                 604

<210> SEQ ID NO 7
<211> LENGTH: 631
<212> TYPE: DNA
<213> ORGANISM: Aphis glycines

<400> SEQUENCE: 7
gttctgggaa atcatttctg atgaacacgg cattgaccca actggagcct accatggaga     60
ctctgatctc caattggaac gtattaatgt atactacaat gaagcctcag gtggaaagta    120
tgtaccccgt gccatcttgg tcgatttgga acctggtacc atggattccg tcagatctgg    180
accattcggt caaattttca gaccagacaa ctttgtcttc ggacagtctg gtgctggaaa    240
caattgggcc aaaggtcatt acacagaagg tgctgagctt gtagattcag tattagatgt    300
tgtcaggaaa gaagctgaga gctgtgattg tcttcaaggt ttccaattga cacattcctt    360
gggtggtggt accggttctg gtatgggaac cttattgatc tccaaaatcc gtgaagaata    420
ccctgacaga attatgaaca catactctgt tgtaccctct cctaaagtat cagacactgt    480
tgtagaaccc tacaatgcta ctctttcagt tcaccaattg gttgaaaata ctgatgaaac    540
ctattgtatt gacaacgaag ccttgtatga catttgcttc cgtacattaa aactcacaac    600
accaacatat ggtgacttaa accacttggt c                                   631

<210> SEQ ID NO 8
<211> LENGTH: 615
<212> TYPE: DNA
<213> ORGANISM: Aphis glycines

<400> SEQUENCE: 8
aagtgttatt ctgcggcgga cgtcgggcgt tgtattcata ttctctctga tcgtgtgtgt     60
gagtaattta ccgcaaaaac ccggattctg taccgttttt cgcccgttaa agcgataaac    120
gtttattaca ctcgtaaaaa ctaattttaa ttgtaaatcg gtccgaaatg gcatcgggag    180
taaccgtagc ggatgcgtgc aaaaaggtct acgaggagat caaaaaggac aagaagcaca    240
ggtacgtggt gtttcacatc aaggacgaga agcagatcga catcgaagtc atcggcgagc    300
gtaactctac ttatgacctg ttcctagaag acctacaaaa ggccggcccg caagaatgcc    360
gttacggtct atttgacttt gagtacactc ccagtgtcta aggcacgtcc gagagctcaa    420
agaagcaaaa gctcttcttg ctttgctggt gcccagacac agctaaagta aagaagaaga    480
tggtctactc atccagctac gacgcgctca gaaatcact ggttggcgta cacaaggcgt    540
tccaggctac tgaccattcg gaagcttccc aagaagtcat cgaggagaag ctcaggtcca    600
ccgacagaca gtaaa                                                     615

<210> SEQ ID NO 9
<211> LENGTH: 612
```

```
<212> TYPE: DNA
<213> ORGANISM: Aphis glycines
<220> FEATURE:
<221> NAME/KEY: misc_feature
<222> LOCATION: 611, 612
<223> OTHER INFORMATION: n = A,T,C or G

<400> SEQUENCE: 9
cggtccgctt cgatgtatat acgcgcaacc ggcggtcgtt agtgcggttt ttttatcgt      60
tttaacgtat atatatatat atatttatat atattatata tgtacatgta tatacacaag    120
taataatata cacagcaaaa gtaaaatat atataattgt attatataaa tatatacagc     180
cagtgtttta aataccgatc taccgtcgca aagaatcgta aaaagaaaaa ttgtttttca    240
tttgaaaata tattcggtac atttttctat ggtgcaccgt ccggtagttg tagtaccgtc    300
gagataactc ctttgaatat cgaactctaa acgcattcgt cgacgaccgt cgcgaagtaa    360
taaaacaccc gcagtgctgt ttccaaatga tgaccatgaa caaccattcg aacgacatcg    420
actacagtaa cggatacatg gaaccggaag aggaatggga acgggaaggg ctgttggacc    480
cagcatggga aaaacaacag aaaaagacct ttacagcatg gggcaactcg cacttacgta    540
aagcaggtac agccattgag aacattgaag aggacttccg caatgggctc aaactcatgt    600
tgctccttga nn                                                        612

<210> SEQ ID NO 10
<211> LENGTH: 622
<212> TYPE: DNA
<213> ORGANISM: Aphis glycines
<220> FEATURE:
<221> NAME/KEY: misc_feature
<222> LOCATION: 620, 621, 622
<223> OTHER INFORMATION: n = A,T,C or G

<400> SEQUENCE: 10
taggaccgta gtgccgaaac cgtttagtga ctactaacta gtaaatatga caattttgtt      60
atgctagtaa atactaagta ggtccacaag tacaagtaac atagttggaa cgaacgaaat    120
acgatgactc aatttctacc acccaatttg ttggcgcttt tcgcgccgag ggatccagtc    180
ccttacctgc cgccagttgc caaattaccg cacgagaaga agactcgcgg gtatctgggc    240
gtcggaagtt ttatggattt attcgaagat cccgaagaca ctcctcctcc aacaaaaatt    300
gaaacccgag aagaacgact agaacgccgt cgtcgagaga aggctgaaca ggtagcatac    360
aagttagaac aagaaattgc tttatgggaa ccacattcag ttgcaaacgc tactacagat    420
ccattcaaaa cattatttgt tgctagaatt aattatgata catctgaatc aaaattacga    480
agagaatttg aactttacgg tcctataaaa aagattgttg tcacacataa taagattgat    540
ggtaaaccga gagggtatgc tttcattgag tacgaatatg aacgtgatat gcattctgca    600
tataaacatg ctgatggaan nn                                              622

<210> SEQ ID NO 11
<211> LENGTH: 23
<212> TYPE: DNA
<213> ORGANISM: Aphis glycines

<400> SEQUENCE: 11
aaactatcaa agtagacacc att                                              23

<210> SEQ ID NO 12
<211> LENGTH: 19
<212> TYPE: RNA
<213> ORGANISM: Artificial Sequence
```

```
<220> FEATURE:
<223> OTHER INFORMATION: Primer

<400> SEQUENCE: 12
acuaucaaag uagacacca                                              19

<210> SEQ ID NO 13
<211> LENGTH: 19
<212> TYPE: RNA
<213> ORGANISM: Artificial Sequence
<220> FEATURE:
<223> OTHER INFORMATION: Primer

<400> SEQUENCE: 13
uggugucuac uuugauagu                                              19

<210> SEQ ID NO 14
<211> LENGTH: 23
<212> TYPE: DNA
<213> ORGANISM: Aphis glycines

<400> SEQUENCE: 14
aatcagcacg atgaccctac att                                         23

<210> SEQ ID NO 15
<211> LENGTH: 19
<212> TYPE: RNA
<213> ORGANISM: Artificial Sequence
<220> FEATURE:
<223> OTHER INFORMATION: Primer

<400> SEQUENCE: 15
ucagcacgau gacccuaca                                              19

<210> SEQ ID NO 16
<211> LENGTH: 19
<212> TYPE: RNA
<213> ORGANISM: Artificial Sequence
<220> FEATURE:
<223> OTHER INFORMATION: Primer

<400> SEQUENCE: 16
uguaggguca ucgugcuga                                              19

<210> SEQ ID NO 17
<211> LENGTH: 23
<212> TYPE: DNA
<213> ORGANISM: Aphis glycines

<400> SEQUENCE: 17
aagccaatgt agtgttgaga ctt                                         23

<210> SEQ ID NO 18
<211> LENGTH: 19
<212> TYPE: RNA
<213> ORGANISM: Artificial Sequence
<220> FEATURE:
<223> OTHER INFORMATION: Primer

<400> SEQUENCE: 18
gccaauguag uguugagac                                              19

<210> SEQ ID NO 19
<211> LENGTH: 19
<212> TYPE: RNA
<213> ORGANISM: Artificial Sequence
```

```
<220> FEATURE:
<223> OTHER INFORMATION: Primer

<400> SEQUENCE: 19
gucucaacac uacauuggc                                              19

<210> SEQ ID NO 20
<211> LENGTH: 23
<212> TYPE: DNA
<213> ORGANISM: Aphis glycines

<400> SEQUENCE: 20
aactccaaac gttcagctat ctt                                         23

<210> SEQ ID NO 21
<211> LENGTH: 19
<212> TYPE: RNA
<213> ORGANISM: Artificial Sequence
<220> FEATURE:
<223> OTHER INFORMATION: Primer

<400> SEQUENCE: 21
cuccaaacgu ucagcuauc                                              19

<210> SEQ ID NO 22
<211> LENGTH: 19
<212> TYPE: RNA
<213> ORGANISM: Artificial Sequence
<220> FEATURE:
<223> OTHER INFORMATION: Primer

<400> SEQUENCE: 22
gauagcugaa cguuuggag                                              19

<210> SEQ ID NO 23
<211> LENGTH: 23
<212> TYPE: DNA
<213> ORGANISM: Aphis glycines

<400> SEQUENCE: 23
aatgaaatgc ataagttctc ctt                                         23

<210> SEQ ID NO 24
<211> LENGTH: 19
<212> TYPE: RNA
<213> ORGANISM: Artificial Sequence
<220> FEATURE:
<223> OTHER INFORMATION: Primer

<400> SEQUENCE: 24
ugaaaugcau aaguucucc                                              19

<210> SEQ ID NO 25
<211> LENGTH: 19
<212> TYPE: RNA
<213> ORGANISM: Artificial Sequence
<220> FEATURE:
<223> OTHER INFORMATION: Primer

<400> SEQUENCE: 25
ggagaacuua ugcauuuca                                              19

<210> SEQ ID NO 26
<211> LENGTH: 23
<212> TYPE: DNA
<213> ORGANISM: Aphis glycines
```

<400> SEQUENCE: 26
aagggtaccc acgacggagc att                                        23

<210> SEQ ID NO 27
<211> LENGTH: 19
<212> TYPE: RNA
<213> ORGANISM: Artificial Sequence
<220> FEATURE:
<223> OTHER INFORMATION: Primer

<400> SEQUENCE: 27
ggguacccac gacggagca                                             19

<210> SEQ ID NO 28
<211> LENGTH: 19
<212> TYPE: RNA
<213> ORGANISM: Artificial Sequence
<220> FEATURE:
<223> OTHER INFORMATION: Primer

<400> SEQUENCE: 28
ugcuccgucg uggguaccc                                             19

<210> SEQ ID NO 29
<211> LENGTH: 23
<212> TYPE: DNA
<213> ORGANISM: Aphis glycines

<400> SEQUENCE: 29
aagaaattcg gtttaggatg gtt                                        23

<210> SEQ ID NO 30
<211> LENGTH: 19
<212> TYPE: RNA
<213> ORGANISM: Artificial Sequence
<220> FEATURE:
<223> OTHER INFORMATION: Primer

<400> SEQUENCE: 30
gaaauucggu uuaggaugg                                             19

<210> SEQ ID NO 31
<211> LENGTH: 19
<212> TYPE: RNA
<213> ORGANISM: Artificial Sequence
<220> FEATURE:
<223> OTHER INFORMATION: Primer

<400> SEQUENCE: 31
ccauccuaaa ccgaauuuc                                             19

<210> SEQ ID NO 32
<211> LENGTH: 23
<212> TYPE: DNA
<213> ORGANISM: Aphis glycines

<400> SEQUENCE: 32
aaaggaaaca cgtgtgcttt ctt                                        23

<210> SEQ ID NO 33
<211> LENGTH: 19
<212> TYPE: RNA
<213> ORGANISM: Artificial Sequence
<220> FEATURE:
<223> OTHER INFORMATION: Primer

<400> SEQUENCE: 33
aggaaacacg ugugcuuuc                                              19

<210> SEQ ID NO 34
<211> LENGTH: 19
<212> TYPE: RNA
<213> ORGANISM: Artificial Sequence
<220> FEATURE:
<223> OTHER INFORMATION: Primer

<400> SEQUENCE: 34
gaaagcacac guguuccu                                               19

<210> SEQ ID NO 35
<211> LENGTH: 23
<212> TYPE: DNA
<213> ORGANISM: Aphis glycines

<400> SEQUENCE: 35
aagagaacac tgcaaaatga gtt                                         23

<210> SEQ ID NO 36
<211> LENGTH: 19
<212> TYPE: RNA
<213> ORGANISM: Artificial Sequence
<220> FEATURE:
<223> OTHER INFORMATION: Primer

<400> SEQUENCE: 36
gagaacacug caaaaugag                                              19

<210> SEQ ID NO 37
<211> LENGTH: 19
<212> TYPE: RNA
<213> ORGANISM: Artificial Sequence
<220> FEATURE:
<223> OTHER INFORMATION: Primer

<400> SEQUENCE: 37
cucauuuugc aguguucuc                                              19

<210> SEQ ID NO 38
<211> LENGTH: 23
<212> TYPE: DNA
<213> ORGANISM: Aphis glycines

<400> SEQUENCE: 38
aacaagattc gaagaccctt att                                         23

<210> SEQ ID NO 39
<211> LENGTH: 19
<212> TYPE: RNA
<213> ORGANISM: Artificial Sequence
<220> FEATURE:
<223> OTHER INFORMATION: Primer

<400> SEQUENCE: 39
caagauucga agacccuua                                              19

<210> SEQ ID NO 40
<211> LENGTH: 19
<212> TYPE: RNA
<213> ORGANISM: Artificial Sequence
<220> FEATURE:
<223> OTHER INFORMATION: Primer

```
<400> SEQUENCE: 40
uaagggucuu cgaaucuug                                                    19

<210> SEQ ID NO 41
<211> LENGTH: 23
<212> TYPE: DNA
<213> ORGANISM: Aphis glycines

<400> SEQUENCE: 41
aatttgcaca tggagatgat ctt                                               23

<210> SEQ ID NO 42
<211> LENGTH: 19
<212> TYPE: RNA
<213> ORGANISM: Artificial Sequence
<220> FEATURE:
<223> OTHER INFORMATION: Primer

<400> SEQUENCE: 42
uuugcacaug gagaugauc                                                    19

<210> SEQ ID NO 43
<211> LENGTH: 19
<212> TYPE: RNA
<213> ORGANISM: Artificial Sequence
<220> FEATURE:
<223> OTHER INFORMATION: Primer

<400> SEQUENCE: 43
gaucaucucc augugcaaa                                                    19

<210> SEQ ID NO 44
<211> LENGTH: 23
<212> TYPE: DNA
<213> ORGANISM: Aphis glycines

<400> SEQUENCE: 44
aacgtccata tggagttggt ctt                                               23

<210> SEQ ID NO 45
<211> LENGTH: 19
<212> TYPE: RNA
<213> ORGANISM: Artificial Sequence
<220> FEATURE:
<223> OTHER INFORMATION: Primer

<400> SEQUENCE: 45
cguccauaug gaguugguc                                                    19

<210> SEQ ID NO 46
<211> LENGTH: 19
<212> TYPE: RNA
<213> ORGANISM: Artificial Sequence
<220> FEATURE:
<223> OTHER INFORMATION: Primer

<400> SEQUENCE: 46
gaccaacucc auauggacg                                                    19

<210> SEQ ID NO 47
<211> LENGTH: 23
<212> TYPE: DNA
<213> ORGANISM: Aphis glycines

<400> SEQUENCE: 47
```

-continued aaggaagcaa gtttggagga att                          23

<210> SEQ ID NO 48
<211> LENGTH: 19
<212> TYPE: RNA
<213> ORGANISM: Artificial Sequence
<220> FEATURE:
<223> OTHER INFORMATION: Primer

<400> SEQUENCE: 48
ggaagcaagu uuggaggaa                               19

<210> SEQ ID NO 49
<211> LENGTH: 19
<212> TYPE: RNA
<213> ORGANISM: Artificial Sequence
<220> FEATURE:
<223> OTHER INFORMATION: Primer

<400> SEQUENCE: 49
uuccuccaaa cuugcuucc                               19

<210> SEQ ID NO 50
<211> LENGTH: 23
<212> TYPE: DNA
<213> ORGANISM: Aphis glycines

<400> SEQUENCE: 50
aacgaagaac tgaaacacca att                          23

<210> SEQ ID NO 51
<211> LENGTH: 19
<212> TYPE: RNA
<213> ORGANISM: Artificial Sequence
<220> FEATURE:
<223> OTHER INFORMATION: Primer

<400> SEQUENCE: 51
cgaagaacug aaacaccaa                               19

<210> SEQ ID NO 52
<211> LENGTH: 19
<212> TYPE: RNA
<213> ORGANISM: Artificial Sequence
<220> FEATURE:
<223> OTHER INFORMATION: Primer

<400> SEQUENCE: 52
uugguguuuc aguucuucg                               19

<210> SEQ ID NO 53
<211> LENGTH: 23
<212> TYPE: DNA
<213> ORGANISM: Aphis glycines

<400> SEQUENCE: 53
aacagacttc ggcttggcca gtt                          23

<210> SEQ ID NO 54
<211> LENGTH: 19
<212> TYPE: RNA
<213> ORGANISM: Artificial Sequence
<220> FEATURE:
<223> OTHER INFORMATION: Primer

<400> SEQUENCE: 54
cagacuucgg cuuggccag                                                    19

<210> SEQ ID NO 55
<211> LENGTH: 19
<212> TYPE: RNA
<213> ORGANISM: Artificial Sequence
<220> FEATURE:
<223> OTHER INFORMATION: Primer

<400> SEQUENCE: 55
cuggccaagc cgaagucug                                                    19

<210> SEQ ID NO 56
<211> LENGTH: 23
<212> TYPE: DNA
<213> ORGANISM: Aphis glycines

<400> SEQUENCE: 56
aattggactg atggctatgc gtt                                               23

<210> SEQ ID NO 57
<211> LENGTH: 19
<212> TYPE: RNA
<213> ORGANISM: Artificial Sequence
<220> FEATURE:
<223> OTHER INFORMATION: Primer

<400> SEQUENCE: 57
uuggacugau ggcuaugcg                                                    19

<210> SEQ ID NO 58
<211> LENGTH: 19
<212> TYPE: RNA
<213> ORGANISM: Artificial Sequence
<220> FEATURE:
<223> OTHER INFORMATION: Primer

<400> SEQUENCE: 58
cgcauagcca ucaguccaa                                                    19

<210> SEQ ID NO 59
<211> LENGTH: 23
<212> TYPE: DNA
<213> ORGANISM: Aphis glycines

<400> SEQUENCE: 59
aatcaattcg acgccttcag ttt                                               23

<210> SEQ ID NO 60
<211> LENGTH: 19
<212> TYPE: RNA
<213> ORGANISM: Artificial Sequence
<220> FEATURE:
<223> OTHER INFORMATION: Primer

<400> SEQUENCE: 60
ucaauucgac gccuucagu                                                    19

<210> SEQ ID NO 61
<211> LENGTH: 19
<212> TYPE: RNA
<213> ORGANISM: Artificial Sequence
<220> FEATURE:
<223> OTHER INFORMATION: Primer

<400> SEQUENCE: 61

-continued acugaaggcg ucgaauuga                                            19

<210> SEQ ID NO 62
<211> LENGTH: 23
<212> TYPE: DNA
<213> ORGANISM: Aphis glycines

<400> SEQUENCE: 62
aaaagatact gagctagtga gtt                                       23

<210> SEQ ID NO 63
<211> LENGTH: 19
<212> TYPE: RNA
<213> ORGANISM: Artificial Sequence
<220> FEATURE:
<223> OTHER INFORMATION: Primer

<400> SEQUENCE: 63
aagauacuga gcuagugag                                            19

<210> SEQ ID NO 64
<211> LENGTH: 19
<212> TYPE: RNA
<213> ORGANISM: Artificial Sequence
<220> FEATURE:
<223> OTHER INFORMATION: Primer

<400> SEQUENCE: 64
cucacuagcu caguaucuu                                            19

<210> SEQ ID NO 65
<211> LENGTH: 23
<212> TYPE: DNA
<213> ORGANISM: Aphis glycines

<400> SEQUENCE: 65
aaagatactg agctagtgag ttt                                       23

<210> SEQ ID NO 66
<211> LENGTH: 19
<212> TYPE: RNA
<213> ORGANISM: Artificial Sequence
<220> FEATURE:
<223> OTHER INFORMATION: Primer

<400> SEQUENCE: 66
agauacugag cuagugagu                                            19

<210> SEQ ID NO 67
<211> LENGTH: 19
<212> TYPE: RNA
<213> ORGANISM: Artificial Sequence
<220> FEATURE:
<223> OTHER INFORMATION: Primer

<400> SEQUENCE: 67
acucacuagc ucaguaucu                                            19

<210> SEQ ID NO 68
<211> LENGTH: 23
<212> TYPE: DNA
<213> ORGANISM: Aphis glycines

<400> SEQUENCE: 68
aatgaaacag aaaagcgtga gtt                                       23

```
<210> SEQ ID NO 69
<211> LENGTH: 19
<212> TYPE: RNA
<213> ORGANISM: Artificial Sequence
<220> FEATURE:
<223> OTHER INFORMATION: Primer

<400> SEQUENCE: 69
ugaaacagaa aagcgugag                                            19

<210> SEQ ID NO 70
<211> LENGTH: 19
<212> TYPE: RNA
<213> ORGANISM: Artificial Sequence
<220> FEATURE:
<223> OTHER INFORMATION: Primer

<400> SEQUENCE: 70
cucacgcuuu ucuguuuca                                            19

<210> SEQ ID NO 71
<211> LENGTH: 23
<212> TYPE: DNA
<213> ORGANISM: Aphis glycines

<400> SEQUENCE: 71
aatgctcaag ttaccaaaat gtt                                       23

<210> SEQ ID NO 72
<211> LENGTH: 19
<212> TYPE: RNA
<213> ORGANISM: Artificial Sequence
<220> FEATURE:
<223> OTHER INFORMATION: Primer

<400> SEQUENCE: 72
ugcucaaguu accaaaaug                                            19

<210> SEQ ID NO 73
<211> LENGTH: 19
<212> TYPE: RNA
<213> ORGANISM: Artificial Sequence
<220> FEATURE:
<223> OTHER INFORMATION: Primer

<400> SEQUENCE: 73
cauuuuggua acuugagca                                            19

<210> SEQ ID NO 74
<211> LENGTH: 23
<212> TYPE: DNA
<213> ORGANISM: Aphis glycines

<400> SEQUENCE: 74
aagatacaaa agccgatgta att                                       23

<210> SEQ ID NO 75
<211> LENGTH: 19
<212> TYPE: RNA
<213> ORGANISM: Artificial Sequence
<220> FEATURE:
<223> OTHER INFORMATION: Primer

<400> SEQUENCE: 75
gauacaaaag ccgauguaa                                            19
```

<210> SEQ ID NO 76
<211> LENGTH: 19
<212> TYPE: RNA
<213> ORGANISM: Artificial Sequence
<220> FEATURE:
<223> OTHER INFORMATION: Primer

<400> SEQUENCE: 76
uuacaucggc uuuuguauc                                                    19

<210> SEQ ID NO 77
<211> LENGTH: 23
<212> TYPE: DNA
<213> ORGANISM: Aphis glycines

<400> SEQUENCE: 77
aaatacagcg ttcaaaaacg att                                               23

<210> SEQ ID NO 78
<211> LENGTH: 19
<212> TYPE: RNA
<213> ORGANISM: Artificial Sequence
<220> FEATURE:
<223> OTHER INFORMATION: Primer

<400> SEQUENCE: 78
auacagcguu caaaaacga                                                    19

<210> SEQ ID NO 79
<211> LENGTH: 19
<212> TYPE: RNA
<213> ORGANISM: Artificial Sequence
<220> FEATURE:
<223> OTHER INFORMATION: Primer

<400> SEQUENCE: 79
ucguuuuuga acgcuguau                                                    19

<210> SEQ ID NO 80
<211> LENGTH: 23
<212> TYPE: DNA
<213> ORGANISM: Aphis glycines

<400> SEQUENCE: 80
aatgatttct ttgggattgg gtt                                               23

<210> SEQ ID NO 81
<211> LENGTH: 19
<212> TYPE: RNA
<213> ORGANISM: Artificial Sequence
<220> FEATURE:
<223> OTHER INFORMATION: Primer

<400> SEQUENCE: 81
ugauuucuuu gggauuggg                                                    19

<210> SEQ ID NO 82
<211> LENGTH: 19
<212> TYPE: RNA
<213> ORGANISM: Artificial Sequence
<220> FEATURE:
<223> OTHER INFORMATION: Primer

<400> SEQUENCE: 82
cccaauccca aagaaauca                                                    19

<210> SEQ ID NO 83
<211> LENGTH: 23
<212> TYPE: DNA
<213> ORGANISM: Aphis glycines

<400> SEQUENCE: 83
aatcaggaaa acttctattc ctt                                              23

<210> SEQ ID NO 84
<211> LENGTH: 19
<212> TYPE: RNA
<213> ORGANISM: Artificial Sequence
<220> FEATURE:
<223> OTHER INFORMATION: Primer

<400> SEQUENCE: 84
ucaggaaaac uucuauucc                                                   19

<210> SEQ ID NO 85
<211> LENGTH: 19
<212> TYPE: RNA
<213> ORGANISM: Artificial Sequence
<220> FEATURE:
<223> OTHER INFORMATION: Primer

<400> SEQUENCE: 85
ggaauagaag uuuuccuga                                                   19

<210> SEQ ID NO 86
<211> LENGTH: 23
<212> TYPE: DNA
<213> ORGANISM: Aphis glycines

<400> SEQUENCE: 86
aacgtttgat ttgggtggcc att                                              23

<210> SEQ ID NO 87
<211> LENGTH: 19
<212> TYPE: RNA
<213> ORGANISM: Artificial Sequence
<220> FEATURE:
<223> OTHER INFORMATION: Primer

<400> SEQUENCE: 87
cguuugauuu ggguggcca                                                   19

<210> SEQ ID NO 88
<211> LENGTH: 19
<212> TYPE: RNA
<213> ORGANISM: Artificial Sequence
<220> FEATURE:
<223> OTHER INFORMATION: Primer

<400> SEQUENCE: 88
uggccaccca aaucaaacg                                                   19

<210> SEQ ID NO 89
<211> LENGTH: 23
<212> TYPE: DNA
<213> ORGANISM: Aphis glycines

<400> SEQUENCE: 89
aattgtattt ttggtagacg ctt                                              23

-continued

<210> SEQ ID NO 90
<211> LENGTH: 19
<212> TYPE: RNA
<213> ORGANISM: Artificial Sequence
<220> FEATURE:
<223> OTHER INFORMATION: Primer

<400> SEQUENCE: 90
uuguauuuuu gguagacgc						19

<210> SEQ ID NO 91
<211> LENGTH: 19
<212> TYPE: RNA
<213> ORGANISM: Artificial Sequence
<220> FEATURE:
<223> OTHER INFORMATION: Primer

<400> SEQUENCE: 91
gcgucuacca aaaauacaa						19

<210> SEQ ID NO 92
<211> LENGTH: 5270
<212> TYPE: DNA
<213> ORGANISM: Artificial Sequence
<220> FEATURE:
<223> OTHER INFORMATION: Suppression Construct

<400> SEQUENCE: 92
aattcactgg ccgtcgtttt acaacgtcgt gactgggaaa accctggcgt tacccaactt      60
aatcgccttg cagcacatcc cccttcgcc agctggcgta atagcgaaga ggcccgcacc      120
gatcgccctt cccaacagtt gcgcagcctg aatggcgaat ggcgcctgat gcggtatttt     180
ctccttacgc atctgtgcgg tatttcacac cgcatacgtc aaagcaacca tagtacgcgc     240
cctgtagcgg cgcattaagc gcggcgggtg tggtggttac gcgcagcgtg accgctacac     300
ttgccagcgc cctagcgccc gctccttcg ctttcttccc ttcctttctc gccacgttcg     360
ccggctttcc ccgtcaagct ctaaatcggg ggctcccttt agggttccga tttagtgctt     420
tacggcacct cgaccccaaa aaacttgatt tgggtgatgg ttcacgtagt gggccatcgc     480
cctgatagac ggttttttcgc cctttgacgt tggagtccac gttctttaat agtggactct     540
tgttccaaac tggaacaaca ctcaaccct tctcgggcta ttcttttgat ttataaggga     600
ttttgccgat ttcggcctat tggttaaaaa atgagctgat ttaacaaaaa tttaacgcga     660
attttaacaa atattaacg tttacaattt tatggtgcac tctcagtaca atctgctctg     720
atgccgcata gttaagccag ccccgacacc cgccaacacc cgctgacgcg ccctgacggg     780
cttgtctgct cccggcatcc gcttacagac aagctgtgac cgtctccggg agctgcatgt     840
gtcagaggtt ttcaccgtca tcaccgaaac gcgcgagacg aaagggcctc gtgatacgcc     900
tattttata ggttaatgtc atgataataa tggtttctta gacgtcaggt ggcacttttc     960
ggggaaatgt gcgcggaacc cctatttgtt tattttcta aatacattca aatatgtatc     1020
cgctcatgag acaataaccc tgataaatgc ttcaataata ttgaaaaagg aagagtatga     1080
gtattcaaca tttccgtgtc gcccttattc ccttttttgc ggcattttgc cttcctgttt     1140
ttgctcaccc agaaacgctg gtgaaagtaa aagatgctga agatcagttg ggtgcacgag     1200
tgggttacat cgaactggat ctcaacagcg gtaagatcct tgagagtttt cgccccgaag     1260
aacgtttttcc aatgatgagc acttttaaag ttctgctatg tggcgcggta ttatcccgta     1320
ttgacgccgg gcaagagcaa ctcggtcgcc gcatacacta ttctcagaat gacttggttg     1380
agtactcacc agtcacagaa aagcatctta cggatggcat gacagtaaga gaattatgca     1440

```
gtgctgccat aaccatgagt gataacactg cggccaactt acttctgaca acgatcggag   1500
gaccgaagga gctaaccgct tttttgcaca acatggggga tcatgtaact cgccttgatc   1560
gttgggaacc ggagctgaat gaagccatac caaacgacga gcgtgacacc acgatgcctg   1620
tagcaatggc aacaacgttg cgcaaactat taactggcga actactact ctagcttccc   1680 ggcaacaatt aatagactgg atggaggcgg ataaagttgc aggaccactt ctgcgctcgg   1740
cccttccggc tggctggttt attgctgata aatctggagc cggtgagcgt gggtctcgcg   1800
gtatcattgc agcactgggg ccagatggta agccctcccg tatcgtagtt atctacacga   1860
cggggagtca ggcaactatg gatgaacgaa atagacagat cgctgagata ggtgcctcac   1920
tgattaagca ttggtaactg tcagaccaag tttactcata tatactttag attgatttaa   1980
aacttcattt ttaatttaaa aggatctagg tgaagatcct ttttgataat ctcatgacca   2040
aaatccctta acgtgagttt tcgttccact gagcgtcaga ccccgtagaa aagatcaaag   2100
gatcttcttg agatcctttt tttctgcgcg taatctgctg cttgcaaaca aaaaaaccac   2160
cgctaccagc ggtggtttgt ttgccggatc aagagctacc aactctttt ccgaaggtaa   2220 ctggcttcag cagagcgcag ataccaaata ctgtccttct agtgtagccg tagttaggcc   2280
accacttcaa gaactctgta gcaccgccta catacctcgc tctgctaatc ctgttaccag   2340
tggctgctgc cagtggcgat aagtcgtgtc ttaccgggtt ggactcaaga cgatagttac   2400
cggataaggc gcagcggtcg ggctgaacgg ggggttcgtg cacacagccc agcttggagc   2460
gaacgaccta caccgaactg agatacctac agcgtgagct atgagaaagc gccacgcttc   2520
ccgaagggag aaaggcggac aggtatccgg taagcggcag ggtcggaaca ggagagcgca   2580
cgagggagct ccaggggga aacgcctggt atctttatag tcctgtcggg tttcgccacc   2640
tctgacttga gcgtcgattt ttgtgatgct cgtcaggggg gcggagccta tggaaaaacg   2700
ccagcaacgc ggcctttta cggttcctgg ccttttgctg gccttttgct cacatgttct   2760
ttcctgcgtt atcccctgat tctgtggata accgtattac cgcctttgag tgagctgata   2820
ccgctcgccg cagccgaacg accgagcgca gcgagtcagt gagcgaggaa gcggaagagc   2880
gcccaatacg caaaccgcct ctccccgcgc gttggccgat tcattaatgc agctggcacg   2940
acaggtttcc cgactggaaa gcgggcagtg agcgcaacgc aattaatgtg agttagctca   3000
ctcattaggc accccaggct ttacacttta tgcttccggc tcgtatgttg tgtggaattg   3060
tgagcggata acaatttcac acaggaaaca gctatgacca tgattacgcc aagcttcgga   3120
tttggagcca agtctcataa acgccattgt ggaagaaagt cttgagttgg tggtaatgta   3180
acagagtagt aagaacagag aagagagaga gtgtgagata catgaattgt cgggcaacaa   3240
aaatcctgaa catcttattt tagcaaagag aaagagttcc gagtctgtag cagaagagtg   3300
aggagaaatt taagctcttg gacttgtgaa ttgttccgcc tcttgaatac ttcttcaatc   3360
ctcatatatt cttcttctat gttacctgaa aaccggcatt taatctcgcg ggtttattcc   3420
ggttcaacat ttttttttgtt ttgagttatt atctgggctt aataacgcag gcctgaaata   3480
aattcaaggc ccaactgttt tttttttaa gaagttgctg ttaaaaaaaa aaaaagggaa   3540
ttaacaacaa caacaaaaaa agataaagaa aataataaca attactttaa ttgtagacta   3600
aaaaaacata gatttatca tgaaaaaag agaaagaaa taaaaacttg gatcaaaaaa   3660
aaaaacatac agatcttcta attattaact tttcttaaaa attaggtcct ttttcccaac   3720
aattaggttt agagttttgg aattaaacca aaaagattgt tctaaaaaat actcaaattt   3780
ggtagataag tttccttatt ttaattagtc aatggtagat actttttttt cttttcttta   3840
```

```
ttagagtaga ttagaatctt ttatgccaag tattgataaa ttaaatcaag aagataaact    3900
atcataatca acatgaaatt aaaagaaaaa tctcatatat agtattagta ttctctatat    3960
atattatgat tgcttattct taatgggttg ggttaaccaa gacatagtct taatggaaag    4020 aatcttttt gaacttttc cttattgatt aaattcttct atagaaaga aagaaattat     4080 ttgaggaaaa gtatatacaa aaagaaaaat agaaaaatgt cagtgaagca gatgtaatgg    4140
atgacctaat ccaaccacca ccataggatg tttctacttg agtcggtctt ttaaaaacgc    4200
acggtggaaa atatgacacg tatcatatga ttccttcctt tagtttcgtg ataataatcc    4260
tcaactgata tcttccttt tttgttttgg ctaaagatat tttattctca ttaatagaaa     4320
agacggtttt gggcttttgg tttgcgatat aaagaagacc ttcgtgtgga agataataat    4380
tcatcctttc gtcttttct gactcttcaa tctctcccaa agcctaaagc gatctctgca     4440
aatctctcgc gactctctct ttcaaggtat attttctgat tctttttgtt tttgattcgt    4500
atctgatctc caatttttgt tatgtggatt attgaatctt ttgtataaat tgcttttgac    4560
aatattgttc gtttcgtcaa tccagcttct aaattttgtc ctgattacta agatatcgat    4620
tcgtagtgtt tacatctgtg taatttcttg cttgattgtg aaattaggat tttcaaggac    4680
gatctattca attttgtgt tttctttgtt cgattctctc tgttttaggt ttcttatgtt     4740
tagatccgtt tctctttggt gttgttttga tttctcttac ggcttttgat ttggtatatg    4800
ttcgctgatt ggtttctact tgttctattg ttttatttca gatgcagatc cccgggctca    4860
ctgtgcggtc tctaattctt tccatacttt tcttgctccg gttttcgcgc ggaatggagg    4920
aacggtcgcc ggcgccgaat tggtgcaagt aaagtatgga tagaatcgga ggccgcggtg    4980
aacgcggccg cttgctaccg agctcgaatt ccccgatcg ttcaaacatt tggcaataaa     5040
gtttcttaag attgaatcct gttgccggtc ttgcgatgat tatcatataa tttctgttga    5100
attacgttaa gcatgtaata attaacatgt aatgcatgac gttatttatg agatgggttt    5160
ttatgattag agtcccgcaa ttatacattt aatacgcgat agaaaacaaa atatagcgcg    5220
caaactagga taaattatcg cgcgcggtgt catctatgtt actagatcgg              5270
```

<210> SEQ ID NO 93
<211> LENGTH: 5270
<212> TYPE: DNA
<213> ORGANISM: Artificial Sequence
<220> FEATURE:
<223> OTHER INFORMATION: Suppression Construct

<400> SEQUENCE: 93

```
aattcactgg ccgtcgtttt acaacgtcgt gactgggaaa accctggcgt tacccaactt      60
aatcgccttg cagcacatcc ccctttcgcc agctggcgta atagcgaaga ggcccgcacc     120
gatcgccctt cccaacagtt gcgcagcctg aatggcgaat ggcgcctgat gcggtatttt    180
ctccttacgc atctgtgcgg tatttcacac cgcatacgtc aaagcaacca tagtacgcgc    240
cctgtagcgg cgcattaagc gcggcgggtg tggtggttac gcgcagcgtg accgctacac    300
ttgccagcgc cctagcgccc gctcctttcg ctttcttccc ttcctttctc gccacgttcg    360
ccggctttcc ccgtcaagct ctaaatcggg ggctcccttt agggttccga tttagtgctt    420
tacggcacct cgaccccaaa aaacttgatt tgggtgatgg ttcacgtagt gggccatcgc    480
cctgatagac ggttttcgc cctttgacgt tggagtccac gttctttaat agtggactct     540
tgttccaaac tggaacaaca ctcaacccta tctcggcta ttcttttgat ttataaggga     600
ttttgccgat ttcggcctat tggttaaaaa atgagctgat ttaacaaaaa tttaacgcga    660
```

| | |
|---|---|
| attttaacaa aatattaacg tttacaattt tatggtgcac tctcagtaca atctgctctg | 720 |
| atgccgcata gttaagccag ccccgacacc cgccaacacc cgctgacgcg ccctgacggg | 780 |
| cttgtctgct cccggcatcc gcttacagac aagctgtgac cgtctccggg agctgcatgt | 840 |
| gtcagaggtt ttcaccgtca tcaccgaaac gcgcgagacg aaagggcctc gtgatacgcc | 900 |
| tattttata ggttaatgtc atgataataa tggtttctta cacgtcaggt ggcacttttc | 960 |
| ggggaaatgt gcgcggaacc cctatttgtt tattttcta aatacattca aatatgtatc | 1020 |
| cgctcatgag acaataaccc tgataaatgc ttcaataata ttgaaaaagg aagagtatga | 1080 |
| gtattcaaca tttccgtgtc gcccttattc ccttttttgc ggcattttgc cttcctgttt | 1140 |
| ttgctcaccc agaaacgctg gtgaaagtaa aagatgctga agatcagttg ggtgcacgag | 1200 |
| tgggttacat cgaactggat ctcaacagcg gtaagatcct tgagagtttt cgccccgaag | 1260 |
| aacgttttcc aatgatgagc acttttaaag ttctgctatg tggcgcggta ttatcccgta | 1320 |
| ttgacgccgg gcaagagcaa ctcggtcgcc gcatacacta ttctcagaat gacttggttg | 1380 |
| agtactcacc agtcacagaa aagcatctta cggatggcat gacagtaaga gaattatgca | 1440 |
| gtgctgccat aaccatgagt gataacactg cggccaactt acttctgaca acgatcggag | 1500 |
| gaccgaagga gctaaccgct tttttgcaca acatggggga tcatgtaact cgccttgatc | 1560 |
| gttgggaacc ggagctgaat gaagccatac caaacgacga gcgtgacacc acgatgcctg | 1620 |
| tagcaatggc aacaacgttg cgcaaactat taactggcga actacttact ctagcttccc | 1680 |
| ggcaacaatt aatagactgg atggaggcgg ataaagttgc aggaccactt ctgcgctcgg | 1740 |
| cccttccggc tggctggttt attgctgata atctggagc cggtgagcgt gggtctcgcg | 1800 |
| gtatcattgc agcactgggg ccagatggta agccctcccg tatcgtagtt atctacacga | 1860 |
| cggggagtca ggcaactatg gatgaacgaa atagacagat cgctgagata ggtgcctcac | 1920 |
| tgattaagca ttggtaactg tcagaccaag tttactcata tatactttag attgatttaa | 1980 |
| aacttcattt ttaatttaaa aggatctagg tgaagatcct ttttgataat ctcatgacca | 2040 |
| aaatccctta acgtgagttt tcgttccact gagcgtcaga ccccgtagaa aagatcaaag | 2100 |
| gatcttcttg agatcctttt tttctgcgcg taatctgctg cttgcaaaca aaaaaaccac | 2160 |
| cgctaccagc ggtggtttgt ttgccggatc aagagctacc aactcttttt ccgaaggtaa | 2220 |
| ctggcttcag cagagcgcag ataccaaata ctgtccttct agtgtagccg tagttaggcc | 2280 |
| accacttcaa gaactctgta gcaccgccta catacctcgc tctgctaatc ctgttaccag | 2340 |
| tggctgctgc cagtggcgat aagtcgtgtc ttaccgggtt ggactcaaga cgatagttac | 2400 |
| cggataaggc gcagcggtcg ggctgaacgg ggggttcgtg cacacagccc agcttggagc | 2460 |
| gaacgaccta caccgaactg agatacctac agcgtgagct atgagaaagc gccacgcttc | 2520 |
| ccgaagggag aaaggcggac aggtatccgg taagcggcag ggtcggaaca ggagagcgca | 2580 |
| cgagggagct ccaggggga aacgcctggt atctttatag tcctgtcggg tttcgccacc | 2640 |
| tctgacttga gcgtcgattt ttgtgatgct cgtcaggggg gcggagccta tggaaaaacg | 2700 |
| ccagcaacgc ggcctttta cggttcctgg ccttttgctg ccttttgct cacatgttct | 2760 |
| ttcctgcgtt atcccctgat tctgtggata accgtattac cgcctttgag tgagctgata | 2820 |
| ccgctcgccg cagccgaacg accgagcgca gcgagtcagt gagcgaggaa gcggaagagc | 2880 |
| gcccaatacg caaaccgcct ctccccgcgc gttggccgat tcattaatgc agctggcacg | 2940 |
| acaggtttcc cgactggaaa gcgggcagtg agcgcaacgc aattaatgtg agttagctca | 3000 |
| ctcattaggc accccaggct ttacacttta tgcttccggc tcgtatgttg tgtggaattg | 3060 |

```
tgagcggata acaatttcac acaggaaaca gctatgacca tgattacgcc aagcttcgga    3120
tttggagcca agtctcataa acgccattgt ggaagaaagt cttgagttgg tggtaatgta    3180
acagagtagt aagaacagag aagagagaga gtgtgagata catgaattgt cgggcaacaa    3240
aaatcctgaa catcttattt tagcaaagag aaagagttcc gagtctgtag cagaagagtg    3300
aggagaaatt taagctcttg gacttgtgaa ttgttccgcc tcttgaatac ttcttcaatc    3360
ctcatatatt cttcttctat gttacctgaa accggcatt taatctcgcg ggtttattcc    3420
ggttcaacat ttttttttgtt ttgagttatt atctgggctt aataacgcag gcctgaaata    3480
aattcaaggc ccaactgttt tttttttaa gaagttgctg ttaaaaaaaa aaaagggaa    3540 ttaacaacaa caacaaaaaa agataaagaa aataataaca attactttaa ttgtagacta    3600
aaaaaacata gattttatca tgaaaaaaag agaaagaaa taaaaacttg gatcaaaaaa    3660
aaaaacatac agatcttcta attattaact tttcttaaaa attaggtcct ttttcccaac    3720
aattaggttt agagttttgg aattaaacca aaagattgt tctaaaaaat actcaaattt    3780
ggtagataag tttccttatt ttaattagtc aatggtagat acttttttt cttttcttta    3840 ttagagtaga ttagaatctt ttatgccaag tattgataaa ttaaatcaag aagataaact    3900
atcataatca acatgaaatt aaaagaaaaa tctcatatat agtattagta ttctctatat    3960
atattatgat tgcttattct taatgggttg ggttaaccaa gacatagtct taatggaaag    4020 aatcttttt gaacttttc cttattgatt aaattcttct atagaaaaga aagaaattat    4080
ttgaggaaaa gtatatacaa aaagaaaaat agaaaaatgt cagtgaagca gatgtaatgg    4140
atgacctaat ccaaccacca ccataggatg tttctacttg agtcggtctt ttaaaaacgc    4200
acggtggaaa atatgacacg tatcatatga ttccttcctt tagtttcgtg ataataatcc    4260
tcaactgata tcttcctttt tttgttttgg ctaaagatat tttattctca ttaatagaaa    4320
agacggtttt gggcttttgg tttgcgatat aaagaagacc ttcgtgtgga agataataat    4380
tcatcctttc gtcttttttct gactcttcaa tctctcccaa agcctaaagc gatctctgca    4440
aatctctcgc gactctctct ttcaaggtat attttctgat tctttttgtt tttgattcgt    4500
atctgatctc caattttgt tatgtggatt attgaatctt ttgtataaat tgcttttgac    4560
aatattgttc gtttcgtcaa tccagcttct aaattttgtc ctgattacta agatatcgat    4620
tcgtagtgtt tacatctgtg taatttcttg cttgattgtg aaattaggat tttcaaggac    4680
gatctattca attttgtgt tttctttgtt cgattctctc tgttttaggt ttcttatgtt    4740
tagatccgtt tctctttggt gttgttttga tttctcttac ggcttttgat ttggtatatg    4800
ttcgctgatt ggtttctact tgttctattg ttttattca gatgcagatc cccgggctca    4860
ctgtgcggtc tctaattata cttcaaaatt acatcggccg gttttcgcgc ggaatggagg    4920
aacggtcgcc ggcgccgaat tgggcgatga aattttgaag aataatcgga ggccgcggtg    4980
aacgcggccg cttgctaccg agctcgaatt ccccgatcg ttcaaacatt tggcaataaa    5040
gtttcttaag attgaatcct gttgccggtc ttgcgatgat tatcatataa tttctgttga    5100
attacgttaa gcatgtaata attaacatgt aatgcatgac gttatttatg agatgggttt    5160
ttatgattag agtcccgcaa ttatacattt aatacgcgat agaaaacaaa atatagcgcg    5220
caaactagga taaattatcg cgcgcggtgt catctatgtt actagatcgg                5270
```

<210> SEQ ID NO 94
<211> LENGTH: 5270
<212> TYPE: DNA
<213> ORGANISM: Artificial Sequence
<220> FEATURE:
<223> OTHER INFORMATION: Suppression Construct

<400> SEQUENCE: 94

```
aattcactgg ccgtcgtttt acaacgtcgt gactgggaaa accctggcgt tacccaactt      60
aatcgccttg cagcacatcc cccttcgcc agctggcgta atagcgaaga ggcccgcacc     120
gatcgccctt cccaacagtt gcgcagcctg aatggcgaat ggcgcctgat gcggtatttt    180
ctccttacgc atctgtgcgg tatttcacac cgcatacgtc aaagcaacca tagtacgcgc    240
cctgtagcgg cgcattaagc gcggcgggtg tggtggttac gcgcagcgtg accgctacac    300
ttgccagcgc cctagcgccc gctcctttcg ctttcttccc ttcctttctc gccacgttcg    360
ccggctttcc ccgtcaagct ctaaatcggg ggctcccttt agggttccga tttagtgctt    420
tacggcacct cgaccccaaa aaacttgatt tgggtgatgg ttcacgtagt gggccatcgc    480
cctgatagac ggttttttcgc cctttgacgt tggagtccac gttctttaat agtggactct    540
tgttccaaac tggaacaaca ctcaaccta tctcgggcta ttcttttgat ttataaggga    600
ttttgccgat ttcggcctat tggttaaaaa atgagctgat ttaacaaaaa tttaacgcga    660
attttaacaa aatattaacg tttacaattt tatggtgcac tctcagtaca atctgctctg    720
atgccgcata gttaagccag ccccgacacc cgccaacacc cgctgacgcg ccctgacggg    780
cttgtctgct cccggcatcc gcttacagac aagctgtgac cgtctccggg agctgcatgt    840
gtcagaggtt ttcaccgtca tcaccgaaac gcgcgagacg aaagggcctc gtgatacgcc    900
tatttttata ggttaatgtc atgataataa tggtttctta cgtcaggt ggcacttttc       960
ggggaaatgt gcgcggaacc cctatttgtt tatttttcta atacattca aatatgtatc    1020
cgctcatgag acaataaccc tgataaatgc ttcaataata ttgaaaaagg aagagtatga    1080
gtattcaaca tttccgtgtc gcccttattc cctttttgc ggcattttgc cttcctgttt    1140
ttgctcaccc agaaacgctg gtgaaagtaa aagatgctga agatcagttg ggtgcacgag    1200
tgggttacat cgaactggat ctcaacagcg gtaagatcct tgagagtttt cgccccgaag    1260
aacgttttcc aatgatgagc acttttaaag ttctgctatg tggcgcggta ttatcccgta    1320
ttgacgccgg gcaagagcaa ctcggtcgcc gcatacacta ttctcagaat gacttggttg    1380
agtactcacc agtcacagaa aagcatctta cggatggcat gacagtaaga gaattatgca    1440
gtgctgccat aaccatgagt gataacactg cggccaactt acttctgaca acgatcggag    1500
gaccgaagga gctaaccgct ttttttgcaca acatggggga tcatgtaact cgccttgatc    1560
gttgggaacc ggagctgaat gaagccatac caaacgacga gcgtgacacc acgatgcctg    1620
tagcaatggc aacaacgttg cgcaaactat taactggcga actacttact ctagcttccc    1680
ggcaacaatt aatagactgg atggaggcgg ataaagttgc aggaccactt ctgcgctcgg    1740
cccttccggc tggctggttt attgctgata aatctggagc cggtgagcgt gggtctcgcg    1800
gtatcattgc agcactgggg ccagatggta agccctcccg tatcgtagtt atctacacga    1860
cggggagtca ggcaactatg gatgaacgaa atagacagat cgctgagata ggtgcctcac    1920
tgattaagca ttggtaactg tcagaccaag tttactcata tatactttag attgatttaa    1980
aacttcattt ttaatttaaa aggatctagg tgaagatcct tttgataat ctcatgacca     2040
aaatccctta acgtgagttt tcgttccact gagcgtcaga ccccgtagaa aagatcaaag    2100
gatcttcttg agatcctttt ttctgcgcg taatctgctg cttgcaaaca aaaaaaccac     2160
cgctaccagc ggtggtttgt ttgccggatc aagagctacc aactctttt ccgaaggtaa     2220
ctggcttcag cagagcgcag ataccaaata ctgtccttct agtgtagccg tagttaggcc    2280
```

```
accacttcaa gaactctgta gcaccgccta catacctcgc tctgctaatc ctgttaccag   2340
tggctgctgc cagtggcgat aagtcgtgtc ttaccgggtt ggactcaaga cgatagttac   2400
cggataaggc gcagcggtcg ggctgaacgg ggggttcgtg cacacagccc agcttggagc   2460
gaacgaccta caccgaactg agatacctac agcgtgagct atgagaaagc gccacgcttc   2520
ccgaagggag aaaggcggac aggtatccgg taagcggcag ggtcggaaca ggagagcgca   2580
cgagggagct tccaggggga aacgcctggt atctttatag tcctgtcggg tttcgccacc   2640
tctgacttga gcgtcgattt ttgtgatgct cgtcagggg gcggagccta tggaaaaacg    2700
ccagcaacgc ggccttttta cggttcctgg ccttttgctg ccttttgct cacatgttct    2760 ttcctgcgtt atccctgat tctgtggata accgtattac cgcctttgag tgagctgata    2820
ccgctcgccg cagccgaacg accgagcgca gcgagtcagt gagcgaggaa gcggaagagc   2880
gcccaatacg caaaccgcct ctccccgcgc gttggccgat tcattaatgc agctggcacg   2940
acaggtttcc cgactggaaa gcgggcagtg agcgcaacgc aattaatgtg agttagctca   3000
ctcattaggc accccaggct ttacacttta tgcttccggc tcgtatgttg tgtggaattg   3060
tgagcggata acaatttcac acaggaaaca gctatgacca tgattacgcc aagcttcgga   3120
tttggagcca agtctcataa acgccattgt ggaagaaagt cttgagttgg tggtaatgta   3180
acagagtagt aagaacagag aagagagaga gtgtgagata catgaattgt cgggcaacaa   3240
aaatcctgaa catcttattt tagcaaagag aaagagttcc gagtctgtag cagaagagtg   3300
aggagaaatt taagctcttg gacttgtgaa ttgttccgcc tcttgaatac ttcttcaatc   3360
ctcatatatt cttcttctat gttacctgaa aaccggcatt taatctcgcg ggtttattcc   3420
ggttcaacat ttttttttgtt ttgagttatt atctgggctt aataacgcag gcctgaaata   3480
aattcaaggc ccaactgttt ttttttttaa gaagttgctg ttaaaaaaaa aaaagggaa    3540 ttaacaacaa caacaaaaaa agataaagaa aataataaca attactttaa ttgtagacta   3600
aaaaaacata gattttatca tgaaaaaaag agaaagaaa taaaaacttg gatcaaaaaa    3660
aaaaacatac agatcttcta attattaact tttcttaaaa attaggtcct ttttcccaac   3720
aattaggttt agagttttgg aattaaacca aaaagattgt tctaaaaaat actcaaattt   3780
ggtagataag tttccttatt ttaattagtc aatggtagag actttttttt cttttcttta   3840
ttagagtaga ttagaatctt ttatgccaag tattgataaa ttaaatcaag aagataaact   3900
atcataatca acatgaaatt aaaagaaaaa tctcatatat agtattagta ttctctatat   3960
atattatgat tgcttattct taatgggttg ggttaaccaa gacatagtct taatggaaag   4020 aatcttttt gaactttttc cttattgatt aaattcttct atagaaaaga agaaattat    4080 ttgaggaaaa gtatatacaa aaagaaaaat agaaaatgt cagtgaagca gatgtaatgg    4140
atgacctaat ccaaccacca ccataggatg tttctacttg agtcggtctt ttaaaaacgc   4200
acggtggaaa atatgacacg tatcatatga ttccttcctt tagtttcgtg ataataatcc   4260
tcaactgata tcttccttt tttgttttgg ctaaagatat tttattctca ttaatagaaa    4320
agacggtttt gggcttttgg tttgcgtat aaagaagacc ttcgtgtgga agataataat    4380
tcatcctttc gtcttttct gactcttcaa tctctcccaa agcctaaagc gatctctgca    4440
aatctctcgc gactctctct ttcaaggtat attttctgat tcttttttgtt tttgattcgt   4500 atctgatctc caattttttgt tatgtggatt attgaatctt ttgtataaat tgcttttgac   4560
aatattgttc gtttcgtcaa tccagcttct aaattttgtc ctgattacta agatatcgat   4620
tcgtagtgtt tacatctgtg taattttcttg cttgattgtg aaattaggat tttcaaggac   4680
```

```
gatctattca attttttgtgt tttctttgtt cgattctctc tgttttaggt ttcttatgtt    4740
tagatccgtt tctctttggt gttgttttga tttctcttac ggcttttgat ttggtatatg    4800
ttcgctgatt ggtttctact tgttctattg ttttatttca gatgcagatc cccgggctca    4860
ctgtgcggtc tctaatttct tcaccacttc aatgcacccg gttttcgcgc ggaatggagg    4920
aacggtcgcc ggcgccgaat tggctgcata gaagtggtga tgaaatcgga ggccgcggtg    4980
aacgcggccg cttgctaccg agctcgaatt tccccgatcg ttcaaacatt tggcaataaa    5040
gtttcttaag attgaatcct gttgccggtc ttgcgatgat tatcatataa tttctgttga    5100
attacgttaa gcatgtaata attaacatgt aatgcatgac gttatttatg agatgggttt    5160
ttatgattag agtcccgcaa ttatacattt aatacgcgat agaaaacaaa atatagcgcg    5220
caaactagga taaattatcg cgcgcggtgt catctatgtt actagatcgg               5270
```